(12) United States Patent
Jordan et al.

(10) Patent No.: US 9,084,653 B2
(45) Date of Patent: *Jul. 21, 2015

(54) METHODS FOR USE IN DENTAL ARTICULATION

(75) Inventors: Russell A. Jordan, Rancho Cucamonga, CA (US); James D. Hansen, Pasadena, CA (US); Joseph M. Caruso, Aguadulce, CA (US); Patrick B. Dufour, Austin, TX (US); Baruch Nissenbaum, Ramat Gan (IL)

(73) Assignees: CADENT, LTD. (IL); 3M INNOVATIVE PROPERTIES COMPANY, St. Paul, MN (US)

( * ) Notice: Subject to any disclaimer, the term of this patent is extended or adjusted under 35 U.S.C. 154(b) by 1145 days.

This patent is subject to a terminal disclaimer.

(21) Appl. No.: 11/931,514

(22) Filed: Oct. 31, 2007

(65) Prior Publication Data

US 2008/0057466 A1    Mar. 6, 2008

Related U.S. Application Data

(60) Continuation of application No. 10/012,873, filed on Nov. 6, 2001, now Pat. No. 7,347,690, which is a continuation of application No. 09/705,540, filed on Nov. 3, 2000, now Pat. No. 6,322,359, which is a division of application No. 08/935,238, filed on Sep. 22, 1997, now Pat. No. 6,152,731.

(51) Int. Cl.
*A61C 19/04* (2006.01)
*A61C 11/00* (2006.01)
(Continued)

(52) U.S. Cl.
CPC ............... *A61C 11/00* (2013.01); *A61C 7/002* (2013.01); *A61C 9/004* (2013.01); *A61C 19/045* (2013.01)

(58) Field of Classification Search
CPC .................................................. A61C 19/045
USPC .................... 433/68, 69, 72, 73, 75, 214, 215
See application file for complete search history.

(56) References Cited

U.S. PATENT DOCUMENTS 3,084,438 A   4/1963   Goodfriend
3,200,497 A   8/1965   Goodfriend
(Continued)

FOREIGN PATENT DOCUMENTS

AU   567106      12/1987
DE   3810455     5/1989
(Continued)

OTHER PUBLICATIONS

Baker, HH., "Building, Visualizing, and Computing on Surfaces of Evolution," *IEEE Computer Graphics & Applications*, pp. 31-41 (1988).
(Continued)

*Primary Examiner* — Ralph Lewis
(74) *Attorney, Agent, or Firm* — Volpe and Koenig, P.C.

(57) ABSTRACT

A computer implemented method includes providing a first set of digital data corresponding to an upper arch image of at least a portion of an upper dental arch of a patient, providing a second set of digital data corresponding to a lower arch image of at least a portion of a lower dental arch of the patient, providing bite alignment data representative of the spatial relationship between the upper dental arch and the lower dental arch of the patient, and aligning the upper and lower arch images relative to one another based on the bite alignment data until an aligned upper and lower arch image is attained. The aligned upper and lower arch images are moved towards each other until a first contact point is detected and at least one of the upper and lower arch images is moved relative to the other in one or more directions to a plurality of positions for determining optimal occlusion position of the lower and upper dental arches.

15 Claims, 20 Drawing Sheets

(51) Int. Cl.
    *A61C 7/00* (2006.01)
    *A61C 9/00* (2006.01)
    *A61C 19/045* (2006.01)

(56) References Cited

U.S. PATENT DOCUMENTS

| | | | |
|---|---|---|---|
| 3,218,716 | A | 11/1965 | Stuart |
| 3,464,115 | A | 9/1969 | Baker |
| 4,324,546 | A | 4/1982 | Heitlinger et al. |
| 4,386,405 | A | 5/1983 | Lewin et al. |
| 4,390,028 | A | 6/1983 | Okano et al. |
| 4,402,326 | A | 9/1983 | Okano et al. |
| 4,436,684 | A | 3/1984 | White |
| 4,445,854 | A | 5/1984 | Bekey et al. |
| 4,478,580 | A | 10/1984 | Barrut |
| 4,528,627 | A | 7/1985 | Coben |
| 4,611,288 | A | 9/1986 | Duret et al. |
| 4,616,998 | A | 10/1986 | Wong |
| 4,634,377 | A | 1/1987 | Behrend |
| 4,639,220 | A | 1/1987 | Nara et al. |
| 4,673,352 | A | 6/1987 | Hansen |
| 4,681,539 | A | 7/1987 | Knap |
| 4,742,464 | A | 5/1988 | Duret et al. |
| 4,773,854 | A | 9/1988 | Weber |
| 4,836,778 | A | 6/1989 | Baumrind et al. |
| 4,837,732 | A | 6/1989 | Brandestini et al. |
| 4,859,181 | A | 8/1989 | Neumeyer |
| 4,892,480 | A | 1/1990 | Levandoski |
| 4,935,635 | A | 6/1990 | O'Harra |
| 4,964,770 | A | 10/1990 | Stinbichler et al. |
| 4,997,369 | A | 3/1991 | Shafir |
| 5,011,405 | A | 4/1991 | Lemchen |
| 5,027,281 | A | 6/1991 | Rekow et al. |
| 5,078,599 | A | 1/1992 | Eenboom et al. |
| 5,090,901 | A | 2/1992 | Levandoski |
| 5,121,333 | A | 6/1992 | Riley et al. |
| 5,121,334 | A | 6/1992 | Riley et al. |
| 5,128,870 | A | 7/1992 | Erdman et al. |
| 5,131,844 | A | 7/1992 | Marinaccio et al. |
| 5,139,419 | A | 8/1992 | Andreiko et al. |
| 5,143,086 | A | 9/1992 | Duret et al. |
| 5,176,515 | A | 1/1993 | Andrews |
| 5,184,306 | A | 2/1993 | Erdman et al. |
| 5,237,998 | A | 8/1993 | Duret et al. |
| 5,248,258 | A | 9/1993 | Feldman |
| 5,257,184 | A | 10/1993 | Mushabac |
| 5,257,203 | A | 10/1993 | Riley et al. |
| 5,266,030 | A | 11/1993 | Van Der Zel |
| 5,273,429 | A | 12/1993 | Rekow et al. |
| 5,278,756 | A | 1/1994 | Lemchen et al. |
| 5,320,528 | A | 6/1994 | Alpern et al. |
| 5,338,198 | A | 8/1994 | Wu et al. |
| 5,340,309 | A | 8/1994 | Robertson |
| 5,342,194 | A | 8/1994 | Feldman |
| 5,359,511 | A | 10/1994 | Schroeder et al. |
| 5,368,478 | A | 11/1994 | Andreiko et al. |
| 5,372,502 | A | 12/1994 | Massen et al. |
| 5,395,238 | A | 3/1995 | Andreiko et al. |
| 5,429,502 | A | 7/1995 | Cooper et al. |
| 5,440,393 | A | 8/1995 | Wenz |
| 5,454,717 | A | 10/1995 | Andreiko et al. |
| RE35,169 | E | 3/1996 | Lemchen et al. |
| 5,518,397 | A | 5/1996 | Andreiko et al. |
| 5,533,895 | A | 7/1996 | Andreiko et al. |
| 5,562,448 | A | 10/1996 | Mushabac |
| 5,569,578 | A | 10/1996 | Mushabac |
| 5,575,645 | A | 11/1996 | Jacobs et al. |
| 5,605,459 | A | 2/1997 | Kuroda |
| 5,683,243 | A | 11/1997 | Andreiko et al. |
| 5,738,517 | A | 4/1998 | Keller |
| 5,800,174 | A | 9/1998 | Andersson |
| 5,823,778 | A | 10/1998 | Schmitt et al. |
| 5,828,721 | A | 10/1998 | Schulze-Ganzlin |
| 5,842,858 | A | 12/1998 | Truppe |
| 5,879,158 | A | 3/1999 | Doyle et al. |
| 5,880,962 | A | 3/1999 | Andersson et al. |
| 5,882,192 | A | 3/1999 | Bergersen |
| 6,152,731 | A | 11/2000 | Jordan et al. |
| 6,322,359 | B1 | 11/2001 | Jordan et al. |
| 7,347,690 | B2 * | 3/2008 | Jordan et al. ............ 433/69 |

FOREIGN PATENT DOCUMENTS

| | | |
|---|---|---|
| EP | 502227 | 9/1992 |
| EP | 634150 | 1/1995 |
| IL | 114691 | 7/1995 |
| IL | 118523 | 9/1996 |
| IL | 120867 | 9/1997 |
| IL | 120892 | 9/1997 |
| IL | 121872 | 2/1998 |
| IL | 118523 | 10/2000 |
| JP | 06269468 | 9/1994 |
| JP | 7005608 | 1/1995 |
| JP | 09220237 | 8/1997 |
| JP | 09238960 | 9/1997 |
| JP | 09238963 | 9/1997 |
| WO | 9008512 | 8/1990 |
| WO | 9522299 | 8/1995 |
| WO | WO 95/22299 | 8/1995 |
| WO | 9703622 | 2/1997 |
| WO | 9727817 | 8/1997 |
| WO | 9832394 | 7/1998 |

OTHER PUBLICATIONS

"Comet Optical Digitizing System," Steinbichler Optotechnik GmbH (Jun. 1994).

Kuroda et al., "Three-dimensional dental care analyzing system using laser scanning," *J. Am. Ortho. Dent. Orthop.*, 110, pp. 1-12 (Oct. 1996).

Laurendeau, D. et al., "A Computer-Vision Technique for the Acquisition and Processing of 3-D Profiles of Dental Imprints: An Application in Orthodontics," *IEEE Transactions on Medical Imaging*, 10 pp. 453-461 (1991).

"Sam Art 200 Articulator," pp. 1-22 (1991).

"Sam 2 System Articulator: Manual with Anatomical Face Bow Mounting," *Manual presented by Great Lakes Orthodontics, Ltd.*, pp. 1-34 (1984).

"The Orthos Approach . . . The First Comprehensive Appliance System Designed to Address Common Clinical Problems," Product literature of Ormco Company, 7 pages (undated).

"Biomechanics in Orthodontics," Product literature of Giorgio Fiorelli—Birte Melson, 2 pages (undated).

\* cited by examiner

METHODS FOR USE IN DENTAL ARTICULATION

CROSS REFERENCE TO RELATED APPLICATION

This application is a continuation of U.S. patent application Ser. No. 10/012,873, filed Nov. 6, 2001, now U.S. Pat. No. 7,347,690, which is a continuation of U.S. patent application Ser. No. 09/705,540, filed Nov. 3, 2000, now U.S. Pat. No. 6,322,359, which is a division of U.S. patent application Ser. No. 08/935,238, filed Sep. 22, 1997, now U.S. Pat. No. 6,152,731.

FIELD OF THE INVENTION

The present invention relates to dental articulation. More particularly, the present invention pertains to methods for use in dental articulation which use digital data that corresponds to images of a patient's upper and lower dental arches.

DESCRIPTION OF THE RELATED ART

Dentists, orthodontists, prosthodontists and others engaged in various fields of dentistry often have use for a model or replica of selected areas of a patient's oral cavity. For example, a dentist or prosthodontist may desire to have a model of an area of a patient's oral cavity where one or more teeth are missing or damaged, so that suitable replacement teeth may be made in the lab using the model as a guide. In practice, the replacement teeth may be fitted by trial and error on the model and adjusted in size and shape as needed until a satisfactory size and shape are attained.

As another example, orthodontists often use models of a patient's teeth to study malformations of the teeth and jaws and plan a course of treatment. In some instances, the orthodontist may use models to trial fit one or more orthodontic appliances that will be used in the oral cavity to move teeth to desired positions. In other instances, models may be used to pre-position a set of orthodontic brackets and associated archwires that are later affixed to the patient's actual dental arches by a technique known as indirect bonding. Models are also used by orthodontists as well as other dental practitioners to serve as a permanent record of a patient's teeth before and after treatment, and in some instances at selected intervals during the treatment program.

The use of dental models provides significant advantages for both the dental practitioner and the patient. Models enable the dental practitioner to adjust the shape and size of replacement teeth and tooth restorations, to fabricate custom appliances, to adjust the position of standard appliances (e.g., indirect bonding), to diagnose patient cases, to plan for oral surgery, and for other like purposes, in the practitioner's laboratory or in an outside laboratory as desired and during a time that is most convenient for the dentist or lab personnel. Moreover, such work can be carried out without requiring the patient to wait in the dental chair. For example, once a satisfactory fitting of replacement teeth, restoration or orthodontic appliances is obtained on a patient model, the replacement teeth, restoration or orthodontic appliances can be readily installed in the patient's oral cavity with few or no additional adjustments.

Oftentimes, it has been advantageous to use a mechanical device called an articulator in conjunction with the models to replicate movement of the patient's lower jaw, i.e., mandible, about the temporal mandibular joint or oral hinge axis. Such articulators include, among others, the SAM II brand articulator from Great Lakes Orthodontics, LTD, Buffalo, N.Y.; Hanau articulator available from Henry Shein, Port Washington, N.Y.; articulators available from Whip-Mix Corp. of Louisville, Ky.; articulators available from Panadent of Grand Terrace, Calif.; as well as the articulator described in U.S. Pat. No. 5,320,528. Articulators are useful for the dental practitioner in the study and correction of the patient's occlusion, with the aim of developing the optimal harmonious occlusal relationship of the patient's dentition. The articulator assists in establishing the optimal occlusal relationship by assisting the practitioner in the determination of proper occlusal contacts and optimum cusp-fossa relationships between the teeth of the patient's upper and lower jaws.

In general, conventional articulators use a model of the patient's upper dental arch and a model of the patient's lower dental arch. To obtain the models, an impression of the patient's upper dental arch and lower dental arch is first obtained. To prepare an impression of the upper arch, a quantity of curable dental impression material is placed in an impression tray, and the tray is then positioned in the patient's oral cavity such that the impression material fills and surrounds the teeth vestibule, and adjacent gingival, i.e., gum, regions of the upper arch. Once the impression material has cured to a sufficient degree, the impression material along with the tray is removed from the oral cavity. An impression of the patient's lower dental arch is obtained in a similar manner.

To make a dental model from each impression, a second curable material is poured or otherwise placed in the cured impression material. After the second material has sufficiently cured, the impression material is removed from the resulting models. When made properly, the models provide an accurate physical replica of the patient's upper and lower teeth as well as adjacent portions of the patient's gingiva and attachment mucosa.

In addition to the two dental models, a bite impression of the patient's upper and lower dental arches is obtained. The bite impression is often obtained using a wax bite plate. As the patient's dental arches are closed, an impression of the cusps of the upper and lower dental arches is simultaneously formed on the wax bite plate which serves to record the relative position between the upper and lower dental arch when the jaws are closed.

In addition, a facebow with a bite fork is used to provide a record of the spatial orientation of the patient's upper dental arch to the ear canals, the latter of which are located a certain distance from the patient's mandibular condyles. One method of using a facebow involves placing a compound material such as dental wax or impression material onto all or a portion of one side of a bite fork. Next, the bite fork is positioned in the patient's oral cavity such that the impression compound is in secure contact with some or all of the cusps of the patient's upper teeth to make an impression of such teeth. Next, a facebow is placed into position such that ear pieces of the facebow fit snugly into the patient's outer ear canals. A nasal support connected to the facebow is then adjusted so that the facebow lies parallel to the Frankfort horizontal plane at the same time that the nasal support is resting in the Nasian notch with the nasal support extending along an axis thereof that lies in the patient's sagittal plane.

Next, the patient's jaws are closed onto the bite fork with supporting material such that the impression on the upper side of the bite fork is in snug, complemental engagement with the cusps of the patient's upper teeth. A jig is then connected between the facebow and an arm of the bite fork that extends outwardly from the patient's mouth. The jig includes adjustable connecting arms and couplers which are tightened once the impression on the bite fork is in snug contact with the cusps of the patient's upper teeth and the facebow has not been inadvertently moved from its previous position in parallel relationship to the Frankfort horizontal plane. The bite fork is placed relative to the upper teeth such that it is used to render an imprint of tooth anatomy for relocating the facebow and jig in a mechanical articulator as described below.

The facebow with the jig provides a mechanical record of the spatial orientation of the patient's upper dental arch to the patient's ear canals and thus to the patient's mandibular condyles. The facebow and jig can then be used to properly position the model that replicates the patient's upper dental arch on the dental mechanical articulator. In some cases, the articulator may be provided with mounting adapters so that only the jig and not the facebow is needed to properly position and mount the model of the patient's upper dental arch on the mechanical articulator.

In brief overview, many mechanical articulators include an upper member and a lower member that are connected together by a pair of pivotal couplings (such as ball and socket joints). The model of the upper arch is connected to the upper member of the articulator, while the model of the lower arch is connected to the lower member of the articulator. The pivotal couplings enable the two models to move toward and away from each other to mimic at least certain movements of the patient's jaws.

To mount the model of the patient's upper dental arch onto the articulator, the bite fork and the jig (and the facebow in accordance with some techniques) is connected in secure relationship to predetermined locations of the articulator. The articulator is oriented so that the impressions on the bite fork face in an upwardly direction. Next, the model of the patient's upper dental arch is placed over the bite fork such that the portions of the model replicating the cusps of the teeth are in registration with the impressions on the bite fork. The upper member of the articulator is then brought into position over the model of the patient's upper dental arch and a quantity of curable material is used to fill the space between the model and the upper member in order to securely connect the same together.

Next, the bite fork and jig (along with the facebow, if used) is removed from the articulator and the articulator is inverted. Condylar adjustments are made as necessary to replicate the patient's temporal mandibular joint (TMJ) anatomy and jaw function. The bite impression is then inverted and placed over the model of the upper arch such that the impressions of the cusps of the patient's upper teeth are in registration with the tooth cusps on the model of the patient's upper arch. Subsequently, the model of the patient's lower dental arch is placed on top of the bite impression such that the tooth cusps of the lower dental arch model are in registration with the bite impression of the patient's lower teeth. The upper and lower arch models are held together with elastic elements or modules to stabilize the assembly.

Another quantity of curable material is then placed in the space between the model of the patient's lower dental arch and the lower arm of the articulator. Once the material has hardened, the upper member of the articulator is opened so that the bite impression can be removed. Subsequently, the upper member can be moved relative to the lower member about the pivotal couplings to replicate opening and closing movement of the patient's jaws.

A variety of mechanical dental articulators are available. A semi-adjustable hinge articulator is similar to a simple hinge and simulates only the opening and closing movements of the mandible about a simple hinge axis. Other mechanical articulators are more complex and may include mechanisms that are adjustable in various planes to simulate lateral and protrusive mandibular movement. Moreover, a variety of techniques are known for mounting dental models onto mechanical articulators, and as such the description set out in the foregoing paragraphs represents only one of many such techniques.

As can be appreciated, however, the technique of articulation that is described above is time consuming and must be carefully executed to ensure that the resulting articulation properly simulates motion of the patient's jaws. Mechanical articulators are also costly, and the more complex articulators sometimes require factory readjustment to ensure that the coupling of the upper member to the lower member of the articulator is properly calibrated. For these and other reasons, dental practitioners typically do not spend the time and expense necessary to articulate a patient's dental models unless there is a special need for such articulation.

Recently, increased interest has been directed toward obtaining digitized, three-dimensional images of the teeth and adjacent gingiva of dental patients. Such images provide an advantage over conventional plaster of Paris models because the digitized images can be easily stored in a digital file along with other patient information and accessed as the need arises. For example, an attempt at describing a dental model simulator is shown in U.S. Pat. No. 5,338,198 to Wu et al. entitled "Dental Model Simulator," issued Aug. 16, 1994. Various methods of obtaining such digitized data have been described, such as laser scanning and photogammetry.

Another digitization process for obtaining images of teeth is described in pending Israeli Patent Application Serial No. 114691, filed Jul. 20, 1995 and entitled "Method and System for Acquiring Three-Dimensional Teeth Image." This particular illustrative method acquires a dental image by removing layers of an impression and a dental impression tray, or by removing layers of a model made from such an impression. As each layer is removed, a two-dimensional image is obtained by a video camera of the remaining flat surface. Data representative of the boundaries of the two-dimensional images representing the surfaces of the teeth and adjacent gingiva are stored by a computing system. Once a sufficient number of layers have been removed, the computing system combines the two-dimensional images of the captured layers into a three-dimensional created image that represents at least a portion of the patient's teeth and gingiva, e.g., by creating surfaces between data points of the captured layers. It should be recognized that such a three-dimensional representation includes calculated data that is generated from actual measured data in the creation of such surfaces, as opposed to the actual measured data.

SUMMARY OF THE INVENTION

The present invention is directed toward methods for use in dental articulation that overcome the problems noted above with respect to conventional mechanical articulators. With the availability of digital dental images, the present invention provides various methods and programs for use in dental articulation.

The present invention in its various embodiments is highly advantageous for the dental practitioner, because the articulation can be carried out using a computing system in conjunction with digital dental image data so that neither models of the patient's upper and lower dental arches nor a mechanical articulator such as described above is needed. The present invention enables the practitioner to study the patient's occlusion so that any necessary corrections can be provided to establish proper occlusal contacts and optimum cusp/fossa relationships between the teeth of the patient's upper and lower dental arches as well as providing other advantages that will be apparent to one skilled in the art from the description provided herein.

A computer implemented method of creating a dental model for use in dental articulation according to the present invention includes providing a first set of digital data corresponding to an upper arch image of at least a portion of an upper dental arch of a patient, providing a second set of digital data corresponding to a lower arch image of at least a portion of a lower dental arch of the patient, and providing hinge axis data representative of the spatial orientation of at least one of the upper and lower dental arches relative to a hinge axis of the patient. Bite alignment data representative of the spatial relationship between the upper dental arch and the lower dental arch of the patient is further provided and the upper arch image and the lower arch image are aligned based on the bite alignment data. A reference hinge axis is created relative to the aligned upper and lower arch images based on the hinge axis data.

In one embodiment of the method, the method further includes providing data associated with condyle geometry of the patient. Such condyle geometry data provides limitations on the movement of at least the lower arch image when the arch images are displayed and manipulated to move at least the lower arch image relative to the upper arch image and the reference hinge axis.

In another computer implemented method of creating a dental model for use in dental articulation, the method includes providing a first set of digital data corresponding to an upper arch image in a coordinate system of at least a portion of an upper dental arch of a patient, providing a second set of digital data corresponding to a lower arch image in the coordinate system of at least a portion of a lower dental arch of the patient, and providing hinge axis data representative of the spatial orientation of at least one of the upper and lower dental arches relative to a condylar axis of the patient. A reference hinge axis is created in the coordinate system relative to the upper and lower arch images based on the hinge axis data.

In yet another computer implemented method of creating a dental model for use in dental articulation, the method includes providing a first set of digital data corresponding to an upper arch image of at least a portion of an upper dental arch of a patient, providing a second set of digital data corresponding to a lower arch image of at least a portion of a lower dental arch of the patient, and providing bite alignment data representative of the spatial relationship between the upper dental arch and the lower dental arch of the patient. The upper and lower arch images are moved relative to one another based on the bite alignment data until an aligned upper and lower arch image is attained. Thereafter, the aligned upper and lower arch images are moved towards each other until a first contact point is detected. At least one of the upper and lower arch images are then moved relative to the other in one or more directions to a plurality of positions for determining optimal occlusion position of the lower and upper dental arches.

A computer implemented method of dental articulation is also described. The method includes providing a dental articulation model. The model includes a first set of digital data corresponding to an upper arch image of at least a portion of an upper dental arch of a patient, a second set of digital data corresponding to a lower arch image of at least a portion of a lower dental arch of the patient, and a third set of digital data representative of the spatial orientation of the upper and lower arch images relative to a reference hinge axis. At least the upper and lower arch images are displayed based at least on the first and second sets of digital data and one or more of the first, second, and third sets of digital data are manipulated to move at least one of the upper and lower arch images about the reference hinge axis to simulate movement of the upper and lower dental arches of the patient.

In one embodiment of the method, the model further includes a fourth set of digital data representative of the spatial orientation of condyle geometry of the patient relative to the reference hinge axis. The manipulation of the digital data may then include manipulation of one or more of the first, second, third and fourth sets of digital data to move at least the lower arch image relative to the upper arch image and the reference hinge axis.

In another computer implemented method of dental articulation, another set of digital data representative of an image having at least three points corresponding to at least three identifiable points of the dental articulation model is provided. At least a portion of the dental articulation model registered with the image is displayed based at least in part on the additional set of data. For example, the set of digital data may be representative of any two dimensional or three dimensional image.

In yet another computer implemented method of dental articulation, yet another set of digital data may be provided which is representative of a plurality of motion recordings of the patient's mandible. The dental articulation model is manipulated to move the lower arch image to simulate relative movement of the lower arch of the patient based at least on the fourth set of digital data.

A computer readable medium tangibly embodying a program executable for creating a dental model for use in dental articulation is also provided along with a computer readable medium tangibly embodying a program executable for performing dental articulation. A facebow apparatus for use with the present invention is also described. Other aspects and further details of the present invention are set out in the description below as well as in the accompanying drawings.

BRIEF DESCRIPTION OF THE DRAWINGS

FIG. 11A is a top view of the apparatus; FIG. 11B is a front view of the apparatus, and FIG. 11C is a side view of the apparatus.

DETAILED DESCRIPTION OF THE EMBODIMENTS

The present invention shall be described generally with reference to FIGS. 1-5. Thereafter, the present invention shall be described in further detail with reference to FIGS. 6-16.

As used herein, the terms given below are defined as follows. Bite registration is defined as the location of the upper and lower dental arches of a patient in occlusion (e.g., maximum intercuspation). The occlusal relationship may be based on first point of contact or based on other degrees of interdigitation of the upper and lower dental arches such as interdigitation for providing maximum intercuspation or to a controlled point of contact between the upper and lower dental arches which avoids mandibular shifting (e.g., shifting which may be due to occlusal prematurity).

Articulation is defined as bite registration in addition to the relationship of the upper and lower dental arches to the condyle axis of the patient. Articulation may occur either as simple hinge motion (i.e., simple hinge articulation) about the condyle axis or hinge motion in combination with other motions of the lower arch relative to the upper arch allowed by the condyle geometry of the patient and muscle function (e.g., full articulation in its most complex form allows for all rotational motion and translational motion of the lower arch relative to the upper arch as would be possible in a patient). In other words, with the upper arch being a rigid body connected to the fossas of the patient's cranium and the lower arch being a rigid body connected to the condyles of the patient's mandible, such complex articulation may include all motions (e.g., rotational and/or translational) possible of the mandible relative to the cranium (e.g., 6 degrees of freedom). Articulation may be described using relationships with external references such as, for example, a horizontal reference plane (e.g., the Frankfort horizontal) and/or a vertical reference plane (e.g., sagittal plane).

Also as used herein, measured digital data refers to digital data captured directly from a patient's anatomy in a digital form (e.g., teeth, gums, condyle geometry, etc.) by any method (e.g., stereographs, digitization probes, optical scanning and detection devices, etc.) or captured indirectly from a patient by removing information regarding the patient's anatomy in a nondigital form (e.g., dental impressions, study models, x-rays, etc.) and then digitizing such information by any method (e.g., slicing the impressions and digitizing boundaries, using an optical scanning and detection device, etc.) Calculated digital data, on the other hand, as used herein refers to digital data generated from measured digital data or any other data. Three-dimensional surface data generated using measured digital data is one example of calculated digital data.

Figure 1:
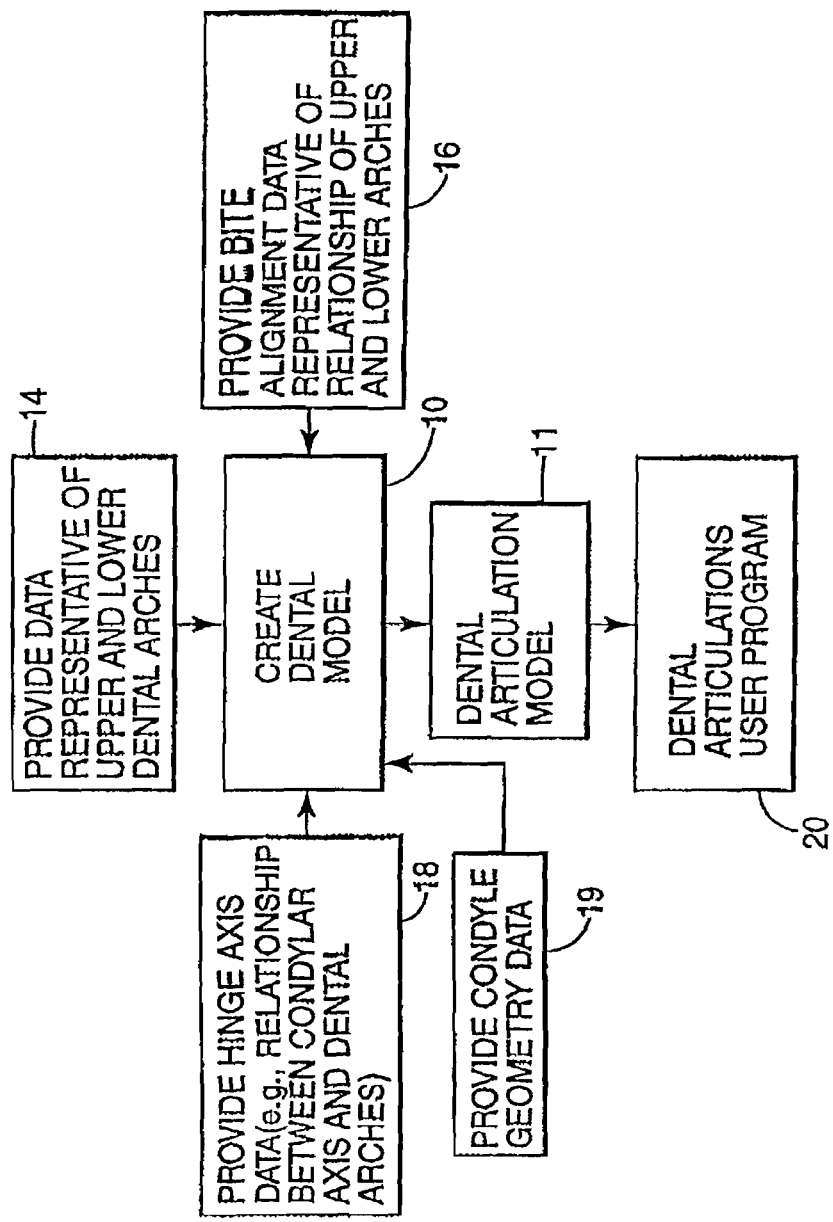
FIG. 1 is block diagram of a dental articulation model creation program in conjunction with a user program for use of a dental articulation model created by the model creation program.

FIG. 1 shows a dental articulation model creation program 10 in conjunction with a user program 20. The model creation program 10 is provided with input data. Such input data at least in part includes digital dental arch data 14 representative of upper and lower dental arches of a patient, bite alignment data 16 representative of the relationship of the upper and lower dental arches of a patient, and hinge axis data 18 representative of the relationship between the upper and/or lower dental arches of the patient and the condyle axis of the patient. Further, condyle geometry digital data 19 representative of condyle geometry of the patient may also be used as further described herein. The model creation program 10 uses this input data to create a dental articulation model 11 which is the output of the dental creation model program 10. The dental articulation model 11 includes at least data representative of images of the upper and lower dental arches of the patient as provided by the dental arch data 14, and relational data representative of the spatial relationship of the dental arch images to one another and further representative of the spatial relationship of the arch images relative to a reference hinge axis corresponding to the condyle axis of the patient. The relational data is determined based on the dental arch data 14, the bite alignment data 16, and the hinge axis data 18.

In many cases, complete orthodontic diagnosis requires detailed knowledge of the geometry of the teeth and soft tissue, i.e., gingiva, that constitute each of the upper and lower dental arches of the patient; the relationship of the dental arches to one another; the relationship of the upper and lower arches to the condyle axis; and the relationship of the dental arches to the skull or parts thereof. Further, the orthodontist may wish to consider the specific geometry of the patient's condyle and the effects of that geometry on the movement of the mandible of the patient. As opposed to the conventional method of representing such information to the orthodontist, i.e., using physical dental models mounted in a mechanical articulator, the present invention captures such information as digital data in the dental articulation model 11 and presents such information to the user, e.g., orthodontist, in displayed three-dimensional image(s), two dimensional view(s), and/or two dimensional projection(s).

Once created, the dental articulation model 11 can be used to present images of the patient's upper and lower dental images, or portions thereof to the user by dental articulation user program 20. For example, the user program 20 can be used to manipulate the displayed articulation model in any manner as would be known to one skilled in the art, and further as specifically described herein. For example, the user program 20 may include routines for performing measurements with reference to the model, routines for manipulation of the orientation of the model as a whole (e.g., the perspective view of all displayed elements being moved in space together), routines for rotating the lower dental arch image relative to a fixed upper dental arch image about a reference hinge axis, routines for movement of the upper dental arch image relative to the reference hinge axis or the lower dental arch image, routines for translational movement of one of the dental arch images as allowed by the condylar geometry of the patient, or routines for detecting virtual contact of one dental arch image with respect to another. It should be apparent to one skilled in the art that the capabilities for movement of objects displayed by a computing system are virtually unlimited and the present invention is not to be limited by any particular user application routine described specifically herein.

Generation of the virtual articulation model 11 generally involves gathering and digitization of the necessary information and thereafter creating the model 11 from such gathered information. The gathering of the necessary information is shown in FIG. 1 as blocks 14, 16, 18 and 19. This information is the input data to the dental creation model program 10.

First, as generally shown by block 14, the data collection process includes capturing the three dimensional morphology of the individual dental arches of the patient. Preferably, such data includes data representative of the structure of all the teeth and the relevant gingiva, but the present invention is also of benefit when one or more portions of such dental arches are captured, e.g., one or more teeth in a section of one of the dental arches. There are a variety of methods available for providing such information and the present invention is not limited to any particular method but only as described in the accompanying claims. For example, tools which can be utilized to provide measured digital data representative of the upper and lower dental arches may include dental impressions, laser scans, stylus scans, and/or stereophotographs. The measured digital data concerning the upper and lower dental arches may be captured directly from the patient in a digital form, e.g., stereographs, or the information may be captured indirectly from the patient by removing the information from the patient in a nondigital form (e.g., dental impressions and study models) and later digitizing the information (e.g., slicing the dental impressions and digitizing the boundaries). Some of the varied processes for providing digitized data of dental arches include, but are clearly not limited to, laser scanning, photogammetry, and those processes described in U.S. Pat. Nos. 5,078,599, 5,131,844, 5,338,198, 4,611,288, 5,372,502, Article entitled "Three-dimensional dental cast analyzing system with laser scanning," by T. Kuroda, et. al., Am. J. Ortho. Dent. Othrop., Vol. 110[4], October 1996, pp. 365-69, and Israeli Patent Application Serial No. 114691 previously cited herein. Preferably, the digital data representative of the dental arches of a patient is provided by the process described in Israeli Patent Application Serial No. 114691 resulting in measured digital data representative of boundaries of sliced portions of dental impressions. Further, such digital data may include calculated data representative of surfaces of the dental arches as opposed to the measured digital data. Such calculated digital data for display of surfaces can be generated in numerous ways from the measured digital data as would be known to one skilled in the art resulting in data representative of various elements used for display of such surfaces, e.g., various calculated points, meshes, polygons, etc.

Second, as generally shown by block 16, the data collection process includes measuring the spatial relationship between the upper and lower dental arches of the patient to provide the bite alignment data necessary to create the dental articulation model 11. There are a variety of methods available for providing such information and the present invention is not limited to any particular method but only as described in the accompanying claims. For example, one method may include identifying at least three nonlinear points on each dental arch and measuring matched pairs of such points, i.e., a pair being one point from each arch. Such measurements may be obtained directly from the patient, i.e., in vivo, or from representations of the dental arches of the patient, such as impressions of the dental arches or dental study models. As another example, alignment features may be added to a model and thereafter digitized with the digitization of the dental arches of the patient. For example, the feature may include one or more points, lines, or planes having common features extending from one dental arch to another. Another tool that may be beneficial for obtaining such information may be a bite impression, such as a silicone or wax bite impression. Further, electronic transducers with digital output are also available such as an instrumented bite fork available under the trade designation of T-Scan from Tekscan, Inc. (Boston, Mass.).

The digital data representative of the dental arches as provided in block 14 and the information defining the relationship between such arches as provided in block 16 can also be captured simultaneously. For example, the arch morphology and the relationship between the arches may be simultaneously captured with use of a double impression. In other words, a double impression may be taken from the patient and thereafter digitized, such as with use of the method described in Israeli Patent Application Serial No. 114691. Several processes for providing such bite alignment data (block 16) will be described further below along with the manner in which the dental model creation program 10 uses such data to create the dental articulation model 11.

Third, as generally shown by block 18, the data collection process includes capturing the spatial relationship between the upper and lower dental arches of the patient and the condyle axis of the patient to provide the hinge axis data necessary to create the dental articulation model 11. There are a variety of methods available for providing such hinge axis data and the present invention is not limited to any particular method but only as described in the accompanying claims. For example, one method may include identifying and measuring the location of at least three nonlinear points on the dental arches relative to the condyle axis. Further, for example, this relationship may be obtained through measurements including facebow transfers (FIGS. 11A-11C) or obtained through the use of cephalometric x-rays. Several processes for providing such hinge axis data (block 16) will be described in more detail below along with the manner in which the dental model creation program 10 uses such data to create the dental articulation model 11.

Optionally, and finally, condyle geometry data may be provided as generally shown by block 19. Condyle geometry can be determined by various registrations (e.g., images, measurements, etc.) of lateral and protrusive excursions of the mandible of the patient and may take various forms. As there are a variety of methods available for providing such information, the present invention is not limited to any particular method but only as described in the accompanying claims.

For example, condyle geometry data 19 may take the form of calculated geometric data of the condyles. Calculated condyle geometry may be created in manners similar to those used for preparing such data for conventional mechanical articulators; many of such techniques being known to those skilled in the art. For example, cephalometric x-rays, tomograms, or magnetic resonance images can be used to obtain such data, as well as methods such as those described in U.S. Pat. No. 4,681,539 to Knap which include forming three dimensional physical recordings (i.e., models) that represent the condyle geometry and which are use in a mechanical articulator to control the motion of physical models of the upper and lower dental arches. Such physical condyle geometry models as described in Knap may be digitized into three dimensional representations of the condyle geometry for use in the present invention as the condyle geometry data 19. Alternatively, the elements of Knap which allow for formation of the physical recordings of the condyle geometry may be replaced with a three dimensional position sensor to digitize the condyle geometry directly as opposed to after the physical recordings of the condyle geometry data are generated. The calculated condyle geometry data may be easily attached, i.e., linked, to the dental articulation model as both include common condyle axis information. Such calculated condyle geometry data provides for limits on the motion of the upper and lower dental arch images of the dental articulation model. For example, motion of such images may be confined to the condyle geometry.

In addition, other data may be used in conjunction with the dental model such as data resulting from recording appropriate motions of the patient during activation of the patient's mandible as described here and in further detail below. At a minimum, such recorded motions may consist of a series of three dimensional positions of three points of the mandible while the maxilla is held in a known fixed position. Such recordings may be made using an Axiograph from Great Lakes Orthodontics of Buffalo, N.Y. or a Sirognathograph from Siemens of Bensheim, Germany. The recorded motions may be captured in computer storage files attached and linked through the common condyle axis to the dental articulation model. The recorded motions can then be played back to show full articulation. The motion files can be supplemented with observational files which may indicate joint clicking and other observations made by a user. The advantage of this recorded motion technique is that geometrical calculation of the condyles is avoided. Further, preservation of the actual movements of the patient's mandible means that all the available information is captured for later analysis. Also, since the dental articulation model is a three-dimensional computer model, the motion of any point on the full articulator can be calculated from the three known points. Therefore, one can calculate and display the traditional pantographic tracings from the three dimensional motion measurements.

Further, excursion information from a base position can be used to capture changes in geometrical relationships of the condyle geometry. For example, the geometrical relationships between the condyle and the fossa can be captured (e.g., by x-ray). The excursion information can then be used to calculate the motion of the condyle in the fossa. This motion information can be used to animate the condyle and fossa image.

Figure 2:
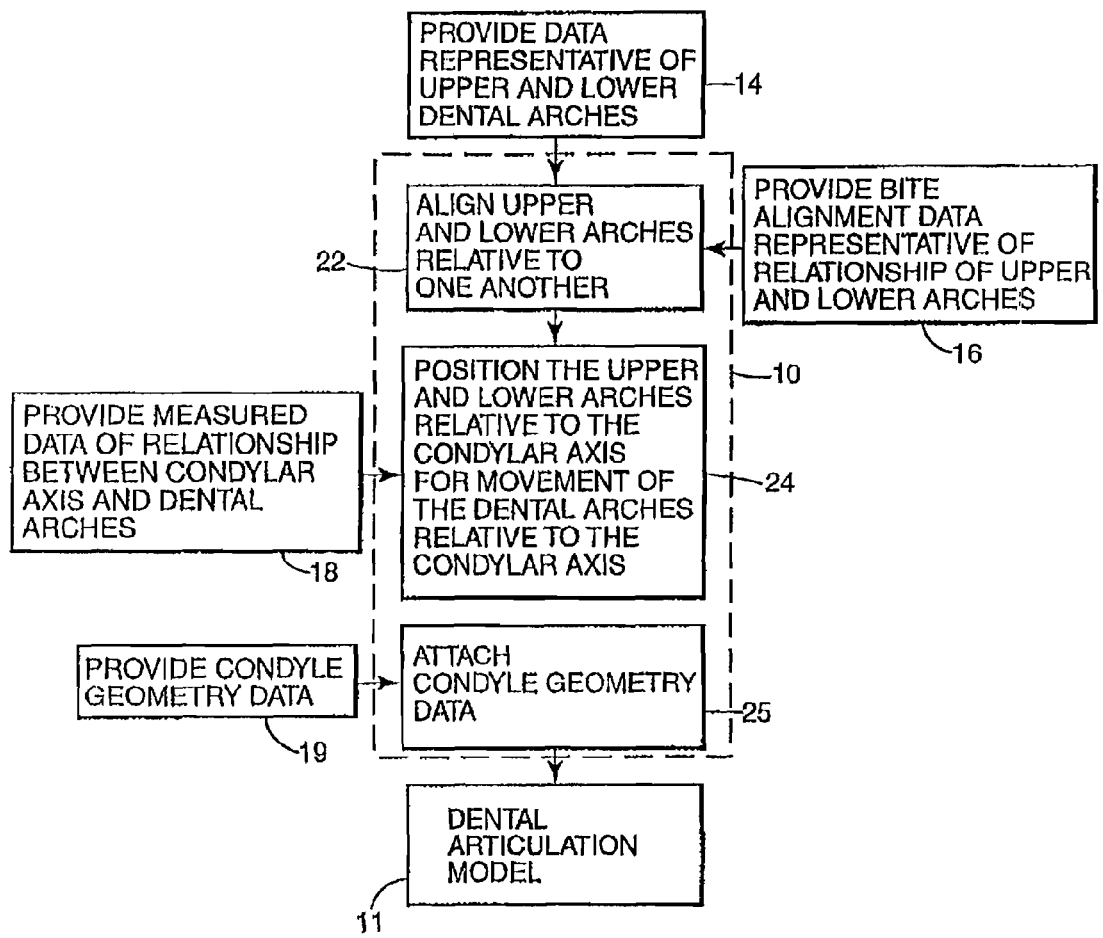
FIG. 2 is a more detailed block diagram of the dental articulation model creation program of FIG. 1.

With the provision of digital data representative of the upper and lower dental arches 14, the provision of the bite alignment data 16, the provision of the hinge axis data 18, and the provision of the optional condyle geometry data 19, the dental creation model program 10 is used to create the dental articulation model 11. As shown in further detail in FIG. 2, the dental articulation model creation program 10 includes alignment routines 22 and hinge axis attachment routines 24 for providing a model suitable for use in simple hinge articulation. Further, FIG. 2 shows in further detail the inclusion of optional condyle geometry attachment routines 25 for providing a model suitable for use in full articulation.

Figure 4:
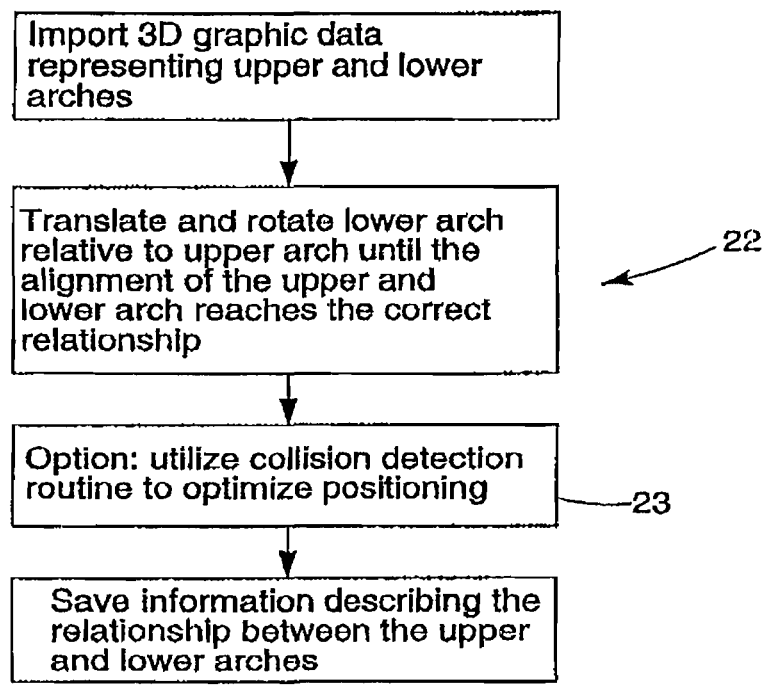
FIG. 4 is a more detailed diagram of an alignment portion of the dental articulation model creation program of FIG. 2.
Figure 5:
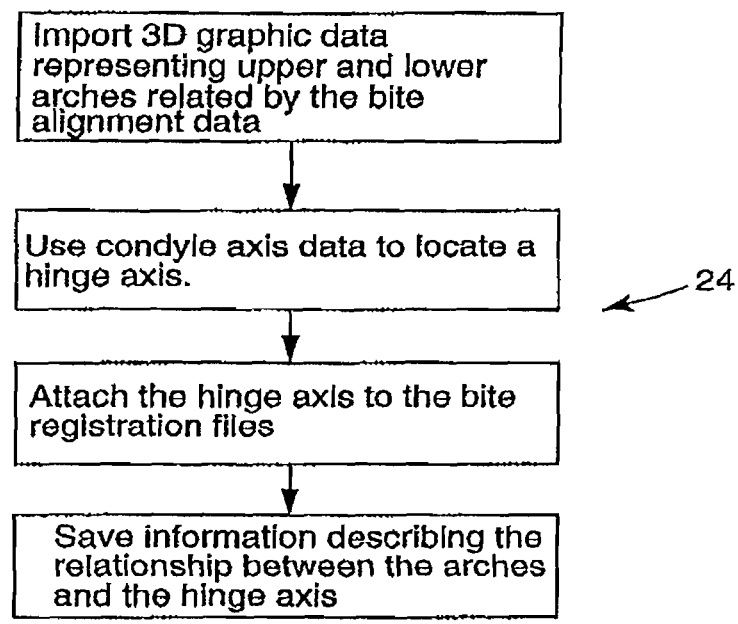
FIG. 5 is more detailed diagram of a hinge axis attachment portion of the dental articulation model creation program of FIG. 2.

Alignment routines 22 manipulate the measured digital data to align the digitized images of the upper and lower dental arches provided per block 14. Generally, as shown in FIG. 4, the digital images (e.g., three dimensional graphic images) are input (e.g., imported from another program) for use by the model creation program 10. The digital data representative of the upper and lower dental arch images is manipulated, e.g., the images translated and rotated, until proper alignment between the upper and lower images is indicated as defined by the bite alignment data (block 16). Further, the measured digital data is manipulated for providing bite registration, i.e., the location of the upper and lower dental arches of the patient in occlusion. Thereafter, the information describing the relationship between the upper and lower dental arches is saved.

Further, as shown in FIG. 4, optionally, the alignment routines 22 may include a centric occlusion bite registration algorithm 23 (described in further detail below with reference to FIGS. 10A-10C) to optimize the position of the upper and lower members in centric occlusion. Portions of the centric occlusion bite registration algorithm 23 provide routines for providing a technique referred to hereinafter as the wobbling technique. Generally, the wobbling technique provides for manipulation of the measured digital data representative of the upper and lower dental arches to move the upper and lower dental arches relative to one another in one or more different directions by relatively small increments, e.g., one or two pixel increments, to optimize the occlusal relationship between the upper and lower dental images. For example, optimal occlusal relationship may include the location of the upper and lower dental arches in maximum or near maximum intercuspation. Further, generally, the wobbling technique is a digital form of processes used in making small adjustments in a mechanical articulator such as when fitting two physical models of the mechanical articulator together. It should be recognized that the centric occlusion bite registration routines are preferably performed using measured digital data as opposed calculated digital data. Thus, the optimized position of the lower and upper dental arches is based on actual measured data as opposed to calculated data generated using such measured data. Calculated data, e.g., generated surface data, may include undesirable additional tolerances from the actual anatomy of the patient.

After the upper and lower dental images have been aligned relative to one another (block 22), the hinge axis attachment routines (block 24) are used to define the spatial relationship between the dental arch images as represented by the digital data of such images (block 14) and the condyle axis of the patient. As shown in the more detailed diagram of FIG. 5, the digital data representative of the upper and lower arch images as aligned and stored (block 22, FIG. 4) is provided as the input to the hinge axis attachment routines 24. The hinge axis data (block 18) is then use to locate a reference hinge axis for the dental articulation model 11 relative to the aligned upper and lower dental arch images. Thereafter, digital data representative of the reference hinge axis is linked or attached to the digital data created and stored by the alignment routines (block 22) and the dental articulation model is stored for further use by the user program 20.

Further, as shown in FIG. 2, the optional condyle geometry attachment routines 25 provide for linking the condyle geometry data 19 to the portions of the dental articulation model as generated by alignment routines (block 22) and hinge axis attachment routines (block 24). Generally, the reference hinge axis of the patient has already been spatially defined in the dental articulation model relative to the upper and lower dental arches. With the condyle axis of the patient being known in the condyle geometry data (block 19), such condyle geometry data 19 can be spatially attached to the dental articulation model using the common condyle axis (i.e., reference hinge axis) feature already spatially defined relative to the upper and lower dental arches. The condyle geometry data 19 may define the limits through which the upper and lower dental arch images can be moved during manipulation by a user. For example, lateral and protrusive excursions of the lower arch may be confined to within the limits of the condyle geometry data as provided in block 19 for the patient. The linked optional condyle geometry data is thus stored in conjunction with the other elements of the dental articulation model 11 for further use with user program 20.

At a minimum, the stored dental articulation model 11 (after the lower and upper arches have been aligned and the hinge axis attached) for simple hinge articulation includes a file structure that describes at least a line corresponding to the condyle axis of the patient (e.g., the line may be represented by end points of the line representative of the center of the condyles) and at least three nonlinear points corresponding to an object rotatable about the condyle axis in the same coordinate system as the condyle axis, e.g., the object being the lower dental arch.

Preferably, the dental articulation model 11 includes a file structure that describes at least a line corresponding to the condyle axis of the patient, at least three nonlinear points corresponding to the lower dental arch in the same coordinate system as the condyle axis, and at least three nonlinear points corresponding to the upper dental arch in the same coordinate system as the condyle axis.

More preferably, the dental articulation model 1 includes a file structure that describes at least a line corresponding to the condyle axis of the patient, points more fully describing the lower dental arch in the same coordinate system as the condyle axis (e.g., points corresponding to the measured digital data of the objects such as the digitized boundaries of the sliced impressions), and points more fully describing the upper dental arch in the same coordinate system as the condyle axis.

Yet more preferably, each of the file structures above may further optionally include the condyle geometry data generated for the patient and which lies in the same coordinate system as the condyle axis. With the dental articulation model 11 including the condyle geometry data, full articulation can be performed when the model is used in conjunction with the user program 20.

One example illustrative of a file structure that describes a dental articulation model 11 is set forth below. In general with respect to the data format, all data in the file structure is standard ASCII characters; all data is organized in lines, terminated with "\n"; the first word in a line is usually the key word associated with the line; some lines do not have keywords, only data; key words that are not recognized are ignored; and lines with text data begin with a colon (:).

Further, the file structure may include two versions of headers: short and long headers. The short header consists of one type of entity: BoundBox. The keyword "BoundBox" is followed by two corners of the bounding box in x, y, z floats. The long header includes various items:

First line: consists of at last the version of the file structure.
  Data lines: each data line begins with a key word; data depends on the keyword; unrecognized keys may be ignored.
  Data Items:
    Bound Box: the keyword "BoundBox" is followed by two corners of the bounding box in x, y, z floats.
    Program: the version of the creating program is written.
    BL: the name of the BL file used to create this 3D file.
  Terminating line: End Header The file structure is divided into several layers. The layers are numbered 0-5 with each layer used to store some graphic elements. For example, the layer 10 may include the contour base data of the dental model (e.g., measured digital data such as the digitized boundaries as previously described herein which form contours if displayed); layer 11 may include draft version of 10; layer 12 may be a low resolution grid (e.g., calculated digital data based on the measured digital data such as meshes); and layers 13-14 may be higher resolution grids.

The various graphic elements may include, for example, three dimensional lines, meshes, and objects; the three dimensional objects may include, for example, object data lines describing control polygons, object sections, point meshes, and point clusters, for use in describing objects such as the lower/upper dental arch, teeth, condyle geometry, etc. Such graphic elements may be provided as follows:

3d Polyline:
    First line: the keyword "Poly3".
    Data lines: a list of 3D polyline points, each point in one line.
    Terminating line: the list is ended by an "EndPoly" statement.
  3d Mesh:
    First line: the keyword "Mesh n m" where n and m are the number of mesh points in x and y directions; this object is a rectangular array of 3D points, interpolated by bilinear interpolation.
    Data lines: flag, x, y, z; if flag is 0, the point data is not displayed (i.e., a hole in the mesh).
    Terminating line: ended by an "EndMesh" statement.
  3d Object (such as Lower/Upper arch, teeth, etc.): each object can contain several items of data.
    First line: Object obj_name; the 3d Object keyword starts an object; for example, special obj_names are lower_arch (for the lower dental arch) and upper_arch (for the upper dental arch).
    Object data lines:
      Control Polygon:
        First lines: ControlPolygon
        Data lines: x y z; where x, y, and z are floating point coordinates of the control polygon.
        Last line: EndPoly
      Data section (a part of a data polyline):
        Data Line: Section cont_num starting_point ending_point; following the keyword section the three integer items refer to a set of points; point are to be taken from a contour (data polygon) cont_num, starting at point starting_point up to (and including) ending_point.
      List of Data sections:
        First line: Sections
        Data Line: cont_num starting_point ending_point; points are to be taken from a contour (data polygon) cont_num, starting at point starting_point up to (and including) ending_point.
        Last line: EndSections
      Point mesh:
        First line: 'Mesh n m', where n and m are the number of mesh points in x and y directions; this object is a rectangular array of 3D points, interpolated by bilinear Interpolation.
        Data lines: flag x y z; if flag is 0, the point data is not displayed (a hole in the mesh)
        Terminating line: EndMesh
      Point cluster (unordered points): this data item contains a set of points and optionally a list of edges and list of faces.

First line: PointCluster n, where n is the number of points in the cluster.
Data lines: x y z, where x, y and z are 3D coordinates of the points.
Separator line: Edges n, where n is the number of edges in the cluster.
Data lines: i j; an edges goes from point i to point j.
Separator line: Faces n, where n is the number of faces in the cluster.
Data lines: i j k l m n; all items are integer indexes of points surrounding a face.
Terminating line: EndCluster
Object's Termination line: EndObject The illustrative file structure will also describe the reference hinge axis, i.e., condyle axis, in the same coordinate system as the other objects of the file structure. The condyle axis defines the axis of rotation of the lower dental arch (object lower-arch) relative to the upper dental arch (object upper_arch). The condyle axis may consist of a key word "tmj_axis" followed by six numbers; the first three numbers define one end point of the axis and the last three numbers define the other end point of the axis. Example: tmj_axis p1 p2 p3 p4 p5 p6.

Further, the illustrative file structure may also describe the condyle geometry in the same manner as the other three-dimensional objects (e.g., dental arches) as described above. Other nongraphic elements may also be included in the file structure. For example, one type of nongraphic element is text.

It will be readily apparent to one skilled in the art that the file structure for the dental articulation model may take many different forms so long as the desired information necessary for performing simple hinge articulation or full articulation as desired is available for use by user program 20. For example, the file structure may include two or more file structures linked to one another. Further, such file structure may also include attached graphical files such as data from a cephalometric x-ray as further described below or a file of recorded mandibular motion for use in playback of mandibular motion using the dental model as further described below.

Figure 3:
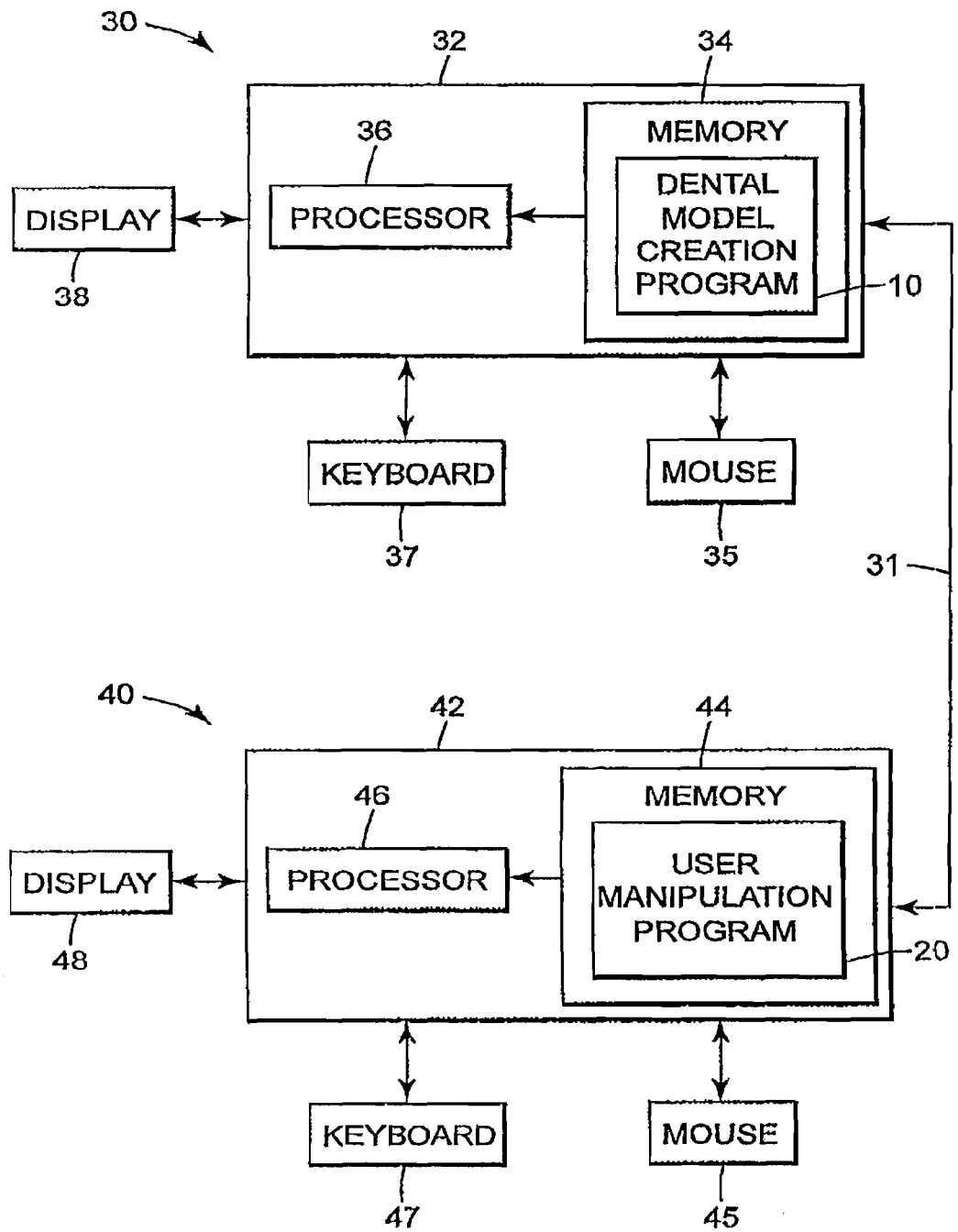
FIG. 3 is a block diagram of an interconnected system for creation of a dental articulation model and for use of the dental articulation model; the system includes memory for storing the programs shown generally in FIG. 1.

As shown in the diagram of FIG. 3, the dental creation program 10 may be resident in memory 34 of a first computing system 30 and the user program 20 may be resident in memory 44 of another computing system 40. However, as would be apparent to one skilled in the art, the programs 10 and 20 may be resident in the memory of the same or different computing systems. It is also readily apparent that the present invention may be adapted to be operable using any processing system, e.g., personal computer, and further, that the present invention is in no manner limited to any particular processing system. The amount of memory of the systems should be sufficient to enable the user to allow for operation of the programs 10, 20 and store data resulting from such operation. It is readily apparent that such memory may be provided by peripheral memory devices to capture the relatively large data/image files resulting from operation of the systems. The systems 30, 40 may include any number of other peripheral devices as desired for operation of the systems 30, 40, such as, for example, the following respective devices: display 38, 48; keyboard 37, 47; and mouse 35, 45. However, it is readily apparent that the system is in no manner limited to use of such devices, nor that such devices are necessarily required for operation of the systems 30, 40.

For example, the computing system 30, 40 may be an HP Vectra-VL with a Matrox Millenium Graphics Card or may be a Netpower Symetra-II with a True-TX Prographics card. However, any suitable computing system may be used. Various programming languages may be used to accomplish the functions as described herein as would be readily apparent to one skilled in the art. For example, such functionality may be provided using C++ language. Further, available software packages may be used for providing various functions as described herein. For example, Open Inventor available from Silicon Graphics may be used to display the dental articulation model to a user. In addition, information may be stored and communicated using digital diagnostic protocol (DDP), commonly known to those skilled in the art.

As shown by the generalized interconnection 31, the information available in either system may be transmitted for use by the other. This interconnection leads to a process that can be implemented for use by a user in a relatively quick manner. For example, the dental articulation model may be created at one location (e.g., such as a lab where impressions are digitized) and thereafter be transmitted back to a dental office for use by an orthodontist; hinge axis data (e.g., such as obtained through a facebow apparatus) may be transmitted to a lab for use in creating the model; or various routines for manipulating the model may be downloaded for use by the user.

Although FIGS. 1 and 2 show the alignment routines 22 and hinge axis attachment routines 24 as being part of a single program and operable as part of a particular computing system, it should be readily apparent that various portions of the program may be resident at multiple locations and various functions carried out at such multiple locations. For example, the hinge axis attachment routines 24 may be resident on a computing system at a user's location. With such a configuration, the alignment may be performed at a first location with the user providing the hinge axis data for input to the system at the user's location. As such, if the hinge axis data is obtained with use of a facebow apparatus, (e.g., such as an apparatus as described herein) the user may input such hinge axis data into the hinge attachment routines of which the alignment data is also an available input. The dental articulation model may then be created immediately at the user's location. The user then has immediate access to a dental articulation model created for a patient.

Various embodiments of processes used in accordance with the present invention shall be further described in more detail with reference to FIGS. 6-16. It should be readily apparent that such embodiments are only illustrative of the various methods which may be used for performing functions in accordance with the present invention. As such, the present invention is not limited to any particular illustrative embodiment as described herein, but only as described in the accompanying claims.

Figure 6A:
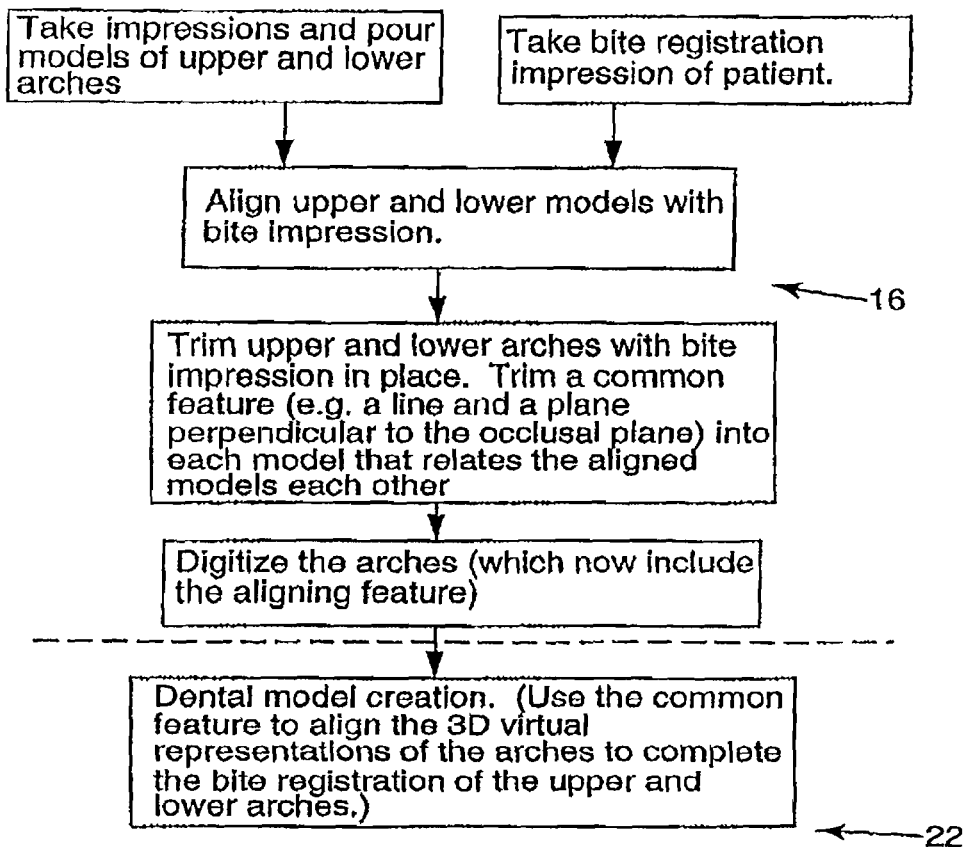
FIGS. 6A-6B show one embodiment of a method for providing bite alignment data for use by the dental articulation model creation program shown in FIG. 1 along with an embodiment of an alignment method using such bite alignment data.
Figure 6B:
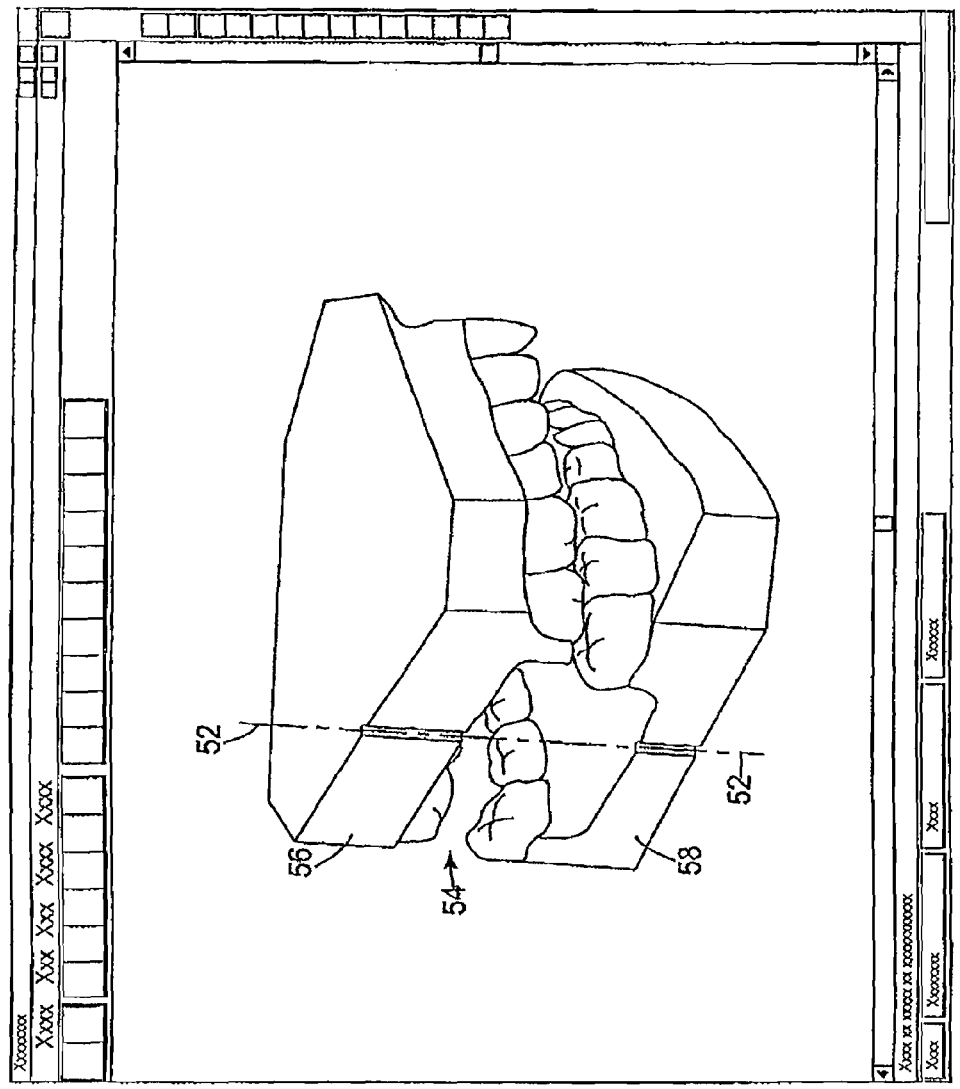
Figure 7:
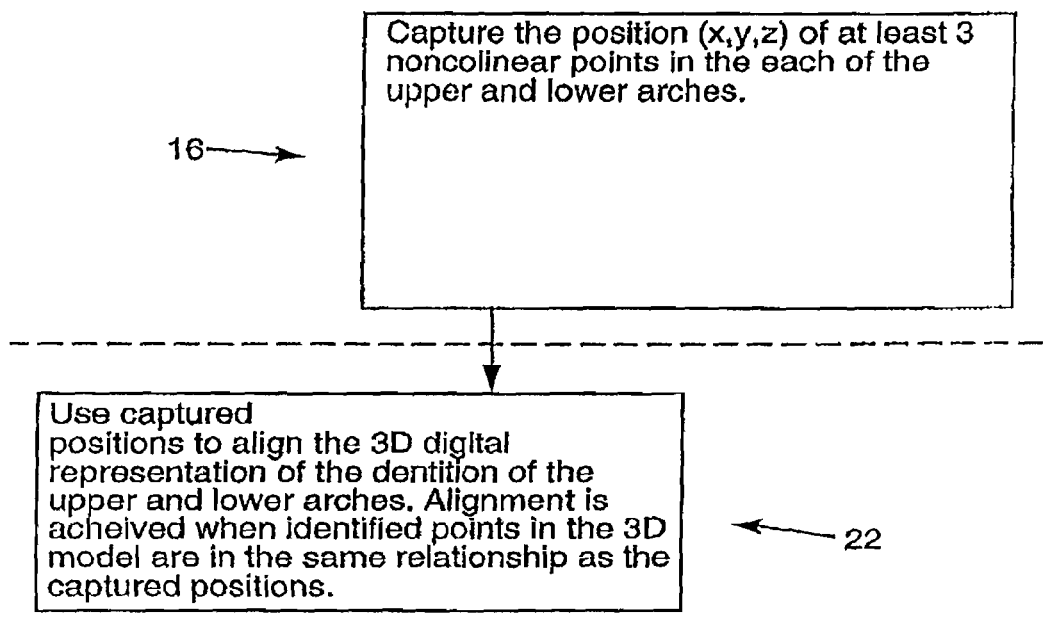
FIG. 7 is another embodiment of a method for providing bite alignment data for use by the dental articulation model creation program shown in FIG. 1 along with an embodiment of an alignment method using such bite alignment data.

FIG. 6 and FIG. 7 show two illustrative embodiments for providing bite alignment data (block 16) according to the present invention. In addition, the FIGS. 6 and 7 show at least portions of the alignment routines (block 22) for aligning the upper and lower arch images using bite alignment data provided in the respective illustrative manners.

As shown in the embodiment of FIG. 6A, provision of bite alignment data includes taking impressions and pouring upper and lower arch models of the upper and lower dental arches of a patient. Further, a bite registration impression, e.g., a wax bite registration, is taken of the patient. The upper and lower arch models are physically aligned using the bite impression positioned therebetween. With the upper and lower arch models maintained in physical alignment with the bite impression, at least one feature common to both the upper and lower dental arch models is trimmed or otherwise formed in the models. The common feature provides the relationship between the upper and lower arch models. For example, the feature may be a line and a plane perpendicular to the occlusal plane, or any other suitable feature or features.

Thereafter, a digital representation of the dental arch models including the alignment feature created in each of the upper and lower dental arches is generated. For example, the digital representation may be provided using any one of the processes as described above as would be known to one skilled in the art.

With the digital data representative of the upper and lower dental arches provided to the model creation program 10 along with the bite alignment data in the form of the digitized alignment feature, the alignment routines 22 are performed as follows. As shown in the display diagram of FIG. 6B, the common features across the upper and lower models is a line segment 52 and a back plane 54 which includes an upper arch back plane 56 and a lower arch back plane 58. With the digital images (including the digitized common feature) input to the alignment routines 22, a point is chosen and the upper arch back plane 56 is placed such that the point is part of the plane 56. Thereafter, the position of the upper back plane 56 is recognized by the program and the lower arch back plane 58 is brought into the same plane as plane 56. With the back planes 56 and 58 aligned, the routines 22 recognize the coordinates of the line segment 52 in the upper back plane 56 and line segment of the lower back plane 58 is aligned with the coordinates. As such, the upper and lower dental images are registered to one another. This aligned data is then stored for use by the hinge axis attachment routines 24.

As shown in FIG. 7, provision of bite alignment data (block 16) includes capturing the spatial coordinates (x, y, z) of at least three identifiable nonlinear points in each of the upper and lower dental arches of the patient (e.g., incisor cusp tip, pits on left and right second molars, etc.). For example, such spatial coordinates may be obtained using a digitizer from Immersion Corp. sold under the trade designation of Microscribe-3DX digitizer and which is equipped with a stylus tip. The spatial coordinates can be captured directly from the patient or from a representation of the patient that contains the relationship of the upper and lower dental arches, e.g., a wax bite impression.

With the digital data representative of the upper and lower dental arches provided to the model creation program 10 along with the spatial coordinates of the at least three nonlinear points in each of the upper and lower dental arches of the patient, the alignment routines 22 are performed as follows. The digital data representative of the upper and lower dental arches is manipulated such that corresponding points of the upper and lower arch images represented by the digital data are in the same spatial relationship as the spatial coordinates of the bite alignment data. In other words, the identifiable points of the upper and lower dental arches of the patient as provided by the bite alignment data and the corresponding identifiable points of the dental arch images are aligned.

Figure 8:
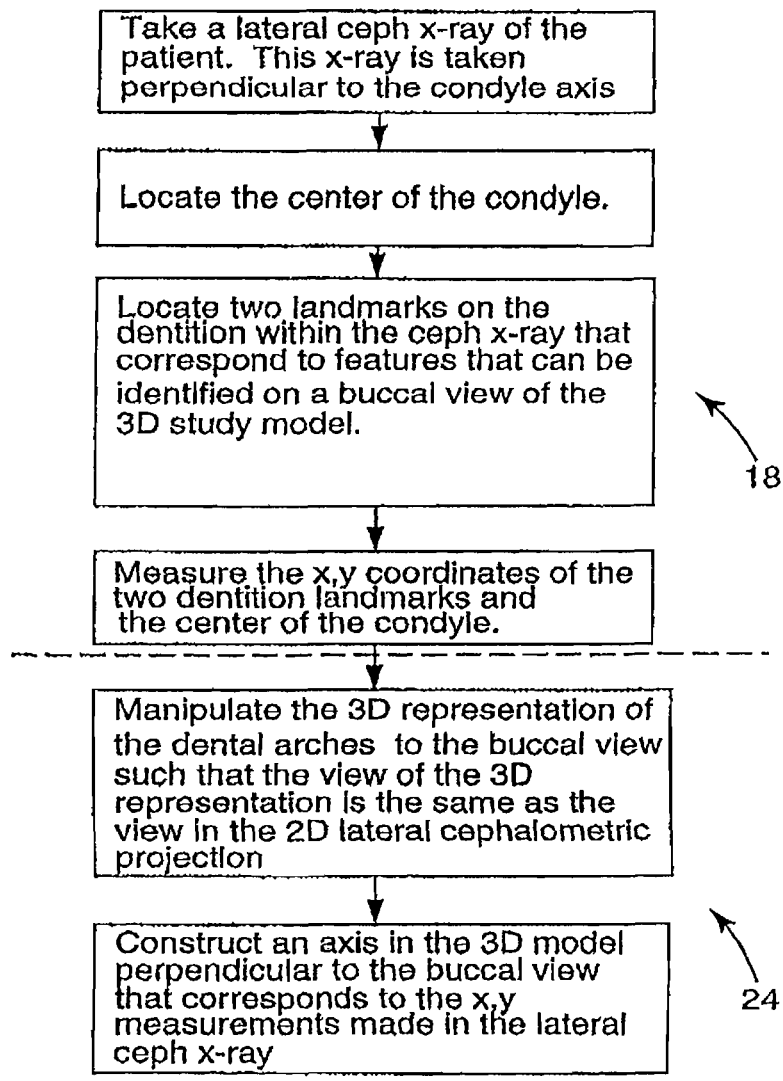
FIG. 8 is one embodiment of a method for providing hinge axis data for use by the dental articulation model creation program shown in FIG. 1 along with an embodiment of an attachment method using such hinge axis data.
Figure 9:
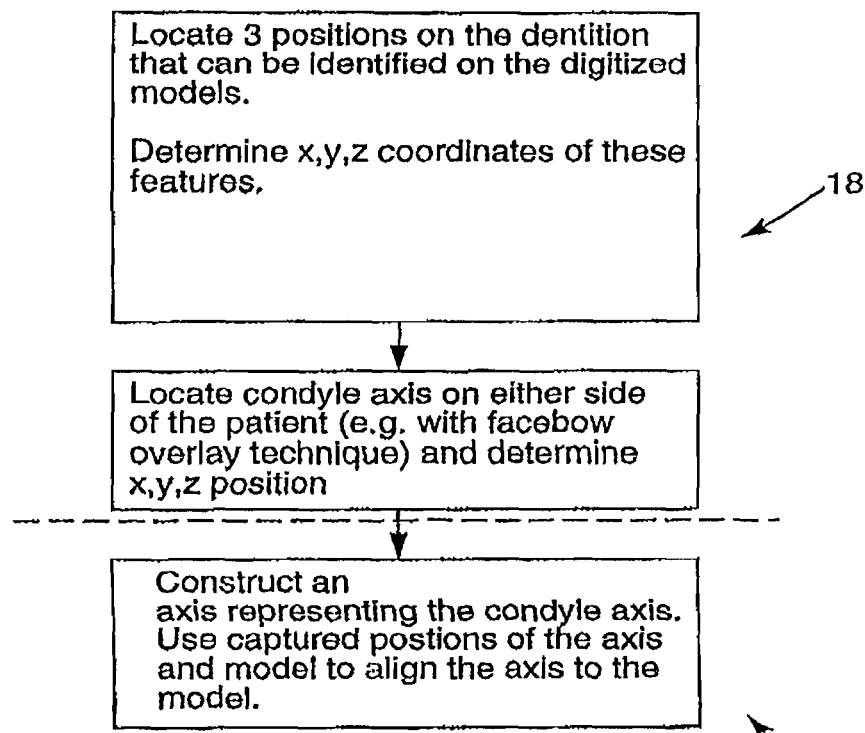
FIG. 9 is another embodiment of a method for providing hinge axis data for use by the dental articulation model creation program shown in FIG. 1 along with an embodiment of an attachment method using such hinge axis data.

FIG. 8 and FIG. 9 show two illustrative embodiments for providing hinge axis data (block 18) according to the present invention. In addition, the FIGS. 8 and 9 show at least portions of the hinge axis attachment routines (block 24) for attaching the reference hinge axis to the aligned upper and lower arch images using hinge axis data provided in the respective illustrative manners.

As shown in FIG. 8, provision of hinge axis data (block 18) includes taking at least a lateral cephalometric x-ray of the patient. The lateral x-ray is taken perpendicular to the condyle axis. The center of the condyle, i.e. the condyle axis, is located on the x-ray. Two identifiable points, i.e., landmarks (e.g., incisor cusp tip, distal surface of the second molar, etc.), on the upper or lower arches are located on the x-ray which have corresponding points that can also be identified on a buccal view of the upper and lower arch images provided by the digital data representative of the upper and lower dental arches of the patient (block 14). The x, y coordinates of the two identifiable points are then measured relative to the center of the condyle, i.e., condyle axis, and provided as the hinge axis data to be used by the dental model creation program 10.

With the digital data representative of the upper and lower dental arches provided to the model creation program 10 along with the hinge axis data, i.e., the x, y coordinates of the identifiable points, the hinge axis attachment routines 24 are performed as follows. The digital data representative of the upper and lower dental arches is manipulated such that the upper and lower dental arch images represented by the digital data are represented in a buccal view corresponding to the laterally taken two-dimensional cephalometric x-ray. Thereafter, the reference hinge axis is constructed in the buccal view and perpendicular thereto using the x,y measurements made for the identifiable points relative to the condyle axis in the x-ray.

As shown in FIG. 9, provision of hinge axis data (block 18) includes capturing the spatial coordinates (x, y, z) of at least three identifiable nonlinear points (e.g., incisor cusp tip, pits on left and right second molars, etc.) on the upper or lower dental arches of the patient. For example, such spatial coordinates may be obtained using a digitizer from Immersion Corp. sold under the trade designation of Microscribe-3DX digitizer equipped with a stylus tip. The spatial coordinates can be captured directly from the patient or from a representation of the patient that contains the relationship of the upper and lower dental arches, e.g., a bite impression. In addition, the condyle axis on either side of the patient is located, e.g., using a facebow overlay technique such as described with reference to the facebow apparatus of FIGS. 11A-11C, and the x, y, z position of the condyle axis is determined. The x, y, and z coordinates of the condyle axis along with the x, y, and z coordinates of the identifiable points of the dental arches are provided as the hinge axis data 18.

Figure 11A:
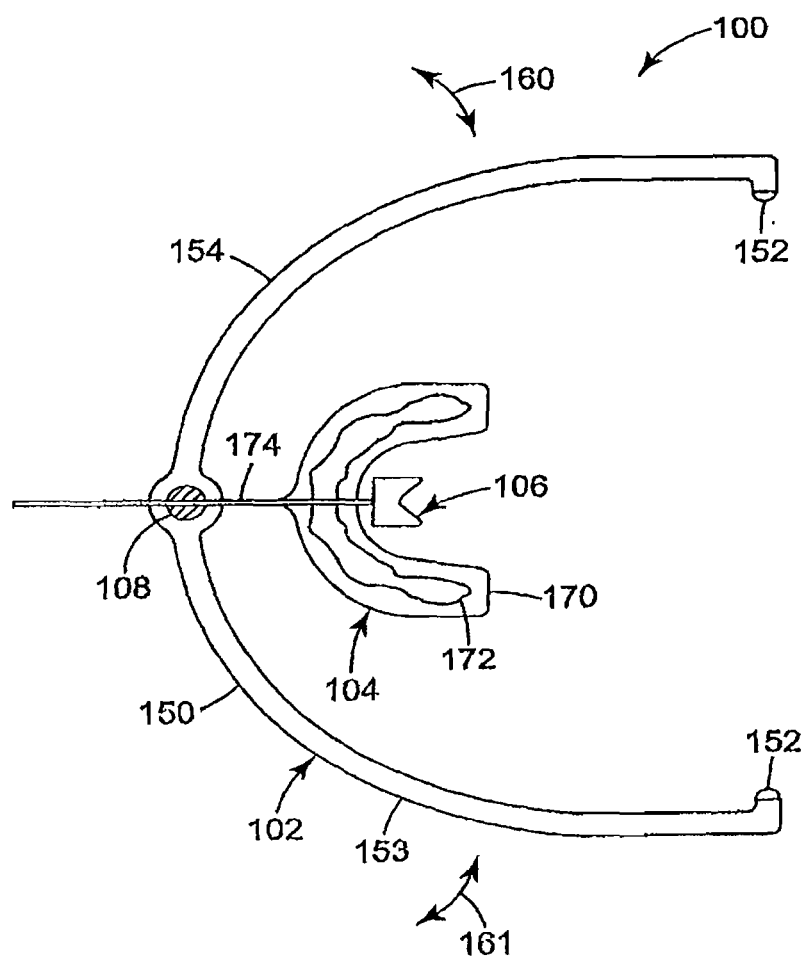
FIGS. 11A-11C illustrate a facebow apparatus for providing hinge axis data for use by the dental articulation model creation program shown in FIG. 1.
Figure 11B:
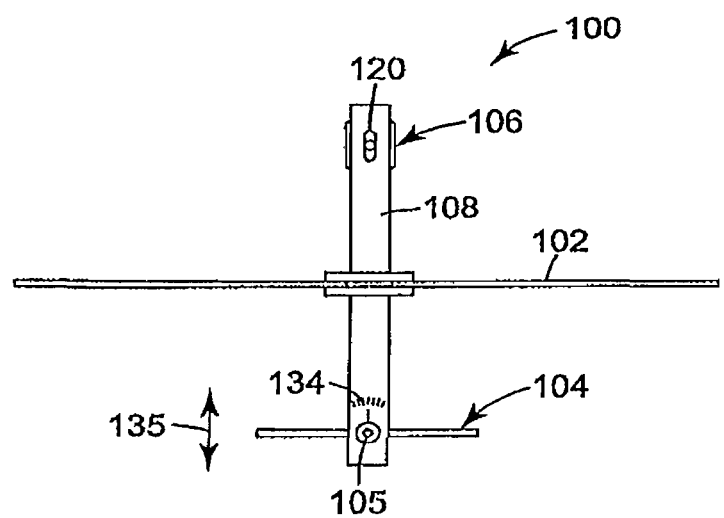
Figure 11C:
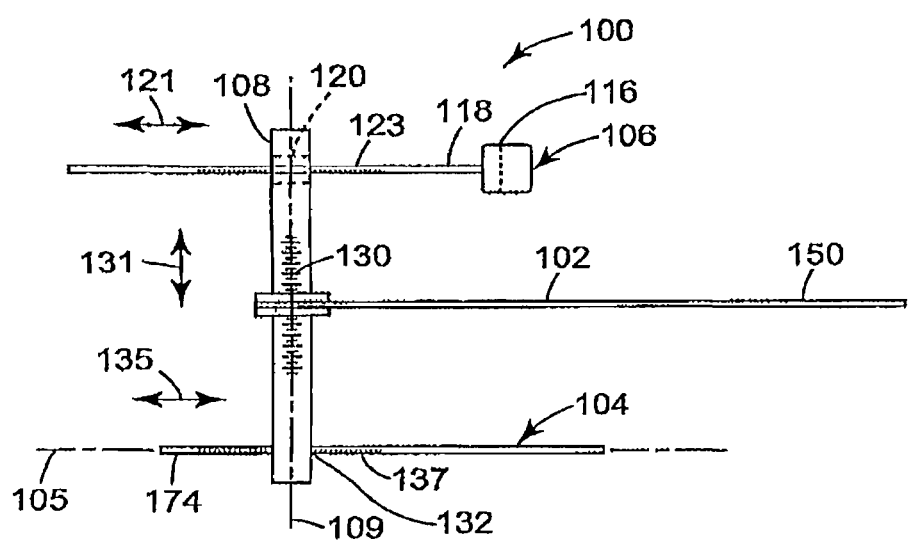

The facebow apparatus 100 as shown in FIGS. 11A-111C can be used to accurately locate at least three positions of the dentition, e.g., cusp tips of the upper arch, and the position of the condyle axis relative to the dentition. Generally, a standard technique is to approximate the condyle axis location as a standard distance from the ear canal. Alternatively, a lateral cephalometric x-ray can provide the relationship between the ear canal and the condyle axis. Therefore, the ear canal effectively locates the condyle axis of a patient. As such, the facebow apparatus uses the relationship between the ear canal and the condyle axis to provide hinge axis data for use according to the present invention.

The facebow apparatus 100 includes a facebow portion 102, a bite fork portion 104, a nasion locator portion 106, which are all adjustably coupled to a post 108. Facebow portion 102 includes an arcuate portion 150 having a first section 153 and a second section 154 which are each separately movable about an axis 109 extending through the post 108 as represented by arrows 160 and 161 respectively. The facebow portion 102 further includes ear canal insertion portions 152 at respective ends of the arcuate portion 150 for engagement with the ear canals of a patient. The facebow portion 102 is adjustable along the axis 109 as represented by double arrow 131. The adjusted position of the facebow portion 102 can be measured by vertical measurement scale section 130 on the post 108.

The bite fork portion 104 includes a bite impression portion 170 which when used is filled with a wax compound or some other impression material 172 capable of retaining the impressions of the cusp tips of the upper dental arch. The bite fork portion 104 further includes a connection member 174 which extends from the bite impression portion 170 and is adjustably coupled through an opening 132 in post 108. As shown by double arrow 135, the bite fork is adjustable perpendicular to the axis 109. Measurement for this adjusted position can be made per measurement scale section 137 on the connection member 174. Further, the bite fork portion 104 is adjustable in an angular manner as shown by double arrow 139 about an axis 105 extending through the connection member 174 of the bite fork portion 104. Such an angular adjusted position can be measured using the angular measurement scale section 134 on post 108.

The nasion locator portion 106 includes a notch portion 116 which is pressed against the bridge of a patient's nose and a locator connection portion 118 which is adjustable coupled to the post 108 through a slot 120. The nasion locator portion 106 is adjustable perpendicular to the axis 108 as shown by double arrow 121. The adjusted position of the nasion locator portion 106 is measured via the measurement scale section 123 on the locator connection member 118.

In general, the position indications as provided by the various measurement scale sections 130, 134, and 137 of the facebow apparatus 100 determine the position and orientation of the bite fork portion 104 with respect to the facebow portion 102. Since the components of the apparatus are all of known dimensions, the measurement data from the measurement scale sections 130, 134, and 137 combined with the location of the cusp tips on the bite plate completely represent the relative locations of the condyle axis and the upper dental arch. The position of the nasion is also referenced to the condyle axis and the dental arches by the measurements of the measurement scale section 123 on the nasion locator 106. It will be recognized that the various movable elements can include any suitable couplings that can be used for adjustment of the elements and/or locking of the movable elements in place.

The facebow apparatus 100 is used in the following manner. The facebow portion 102 via the ear canal insertion portions 152 is placed in the ear canals of a patient. The nasion locator 106 is position in the slot 120 of the post 108 and the notch 116 is pressed against the bridge of the patient's nose. The nasion locator 106 is then locked into place in post 108. The bite fork portion 104 is loaded with impression material 172 and engaged into the post 108. The bite fork portion 104 is positioned to locate the occlusal plane of the upper arch. The bite fork portion 104 is then pressed into the upper arch and the bite fork is locked into place in the post 108.

With the components locked into place, the measurement scale sections 130, 134, and 137 are read and noted. The facebow apparatus 100 is then disassembled and the positions of at least three identifiable cusp tips are measured on the bite fork such as by a three dimensional digitizer. The cusp tip coordinate positions, the measurements noted from the measurement scale sections, and the known dimensions of the facebow apparatus 100 provide the hinge axis data for attachment of a reference hinge axis to the aligned dental arches. It should be apparent to one skilled in the art that electronic transducers may be used in place of the measurement scales such that the data from such transducers could be exported directly to a computer for use in creating the dental model.

With the digital data representative of the upper and lower dental arches provided to the model creation program 10 along with the generated hinge axis data as shown in FIG. 9 (e.g., facebow data), the hinge axis attachment routines 24 are performed as follows. The digital data representative of the upper and lower dental arches is manipulated such that the upper and lower dental arch images represented by the digital data are represented in a view corresponding to the x, y, and z coordinates of the identifiable positions of the dental arches (e.g., the at least three identifiable cusp tips). Thereafter, the reference hinge axis is constructed using the captured x, y, and z coordinates determined for the condyle axis using a technique such as the facebow overlay (e.g., the measurements of the measurement scale sections and the known dimensions of the facebow components).

It will be readily apparent to one skilled in the art that the routines as described with reference to FIGS. 1-9 may or may not require user input. For example, the alignment routines may be initiated by a user selecting for display an upper and lower dental image. Thereafter, the alignment of the upper and lower dental images relative to each other may be performed automatically by the computing system using routines for accomplishing the functionality as described herein. Further, the attachment of the reference hinge axis may be performed automatically upon selection of the applicable hinge axis data to be used for generating the articulation model. For example, with the hinge axis data provided as shown in FIG. 8, the computing system will manipulate the images of the dental arches to a buccal view and then use the x, y coordinates to create the axis, i.e., a line, in the same coordinate system as the manipulated images.

The centric occlusion bite registration algorithm 23 including the wobbling technique as presented summarily above with reference to FIG. 4, shall be described in further detail with reference to FIGS. 10A-10C. The wobbling technique may be used to find the optimal centric occlusal relationship, i.e., determine proper occlusal contacts and optimum cusp-fossa relationships between the teeth of the patient's upper and lower jaws (fossa/cusp interdigitation).

In general, the wobbling technique includes moving images of the upper and lower dental arches aligned along a plane towards each other until a first contact point is detected, i.e., a pixel of the upper dental arch occupies the same coordinate position as a pixel of the lower dental arch. The images are then moved in one or more directions relative to one another in very small increments (preferably of pixel resolution) into a plurality of positions relative to the first contact point. Corresponding pixels of the upper and lower dental arches, i.e., those lying along a similar coordinate axis, are compared to each other at each of the positions to determine which position provides optimal interdigitation between the upper and lower dental arches based on the distance between the corresponding pixels at the plurality of positions. Thereafter, with the first contact point maintained, one of the upper or lower dental arch images may be rotated about an axis through the first contact point and perpendicular to the alignment plane to attain a second point of contact between the upper and lower dental arch images in a region of the dental model symmetrically opposed to the region in which the first contact point resides.

In other words, the dental arch images are moved relative to each other in very small increments, preferably of pixel resolution, to allow for the determination of optimal occlusion of the lower and upper dental arches, i.e. the dental arch images are wobbled relative to one another to determine optimal interdigitation. It will be apparent to one skilled in the art that such movement may be made in one or more directions along one or more coordinate axes or about one or more coordinate axes and that such movement is clearly not limited to the movement of the images as described in the illustrative embodiment below.

Figure 10A:
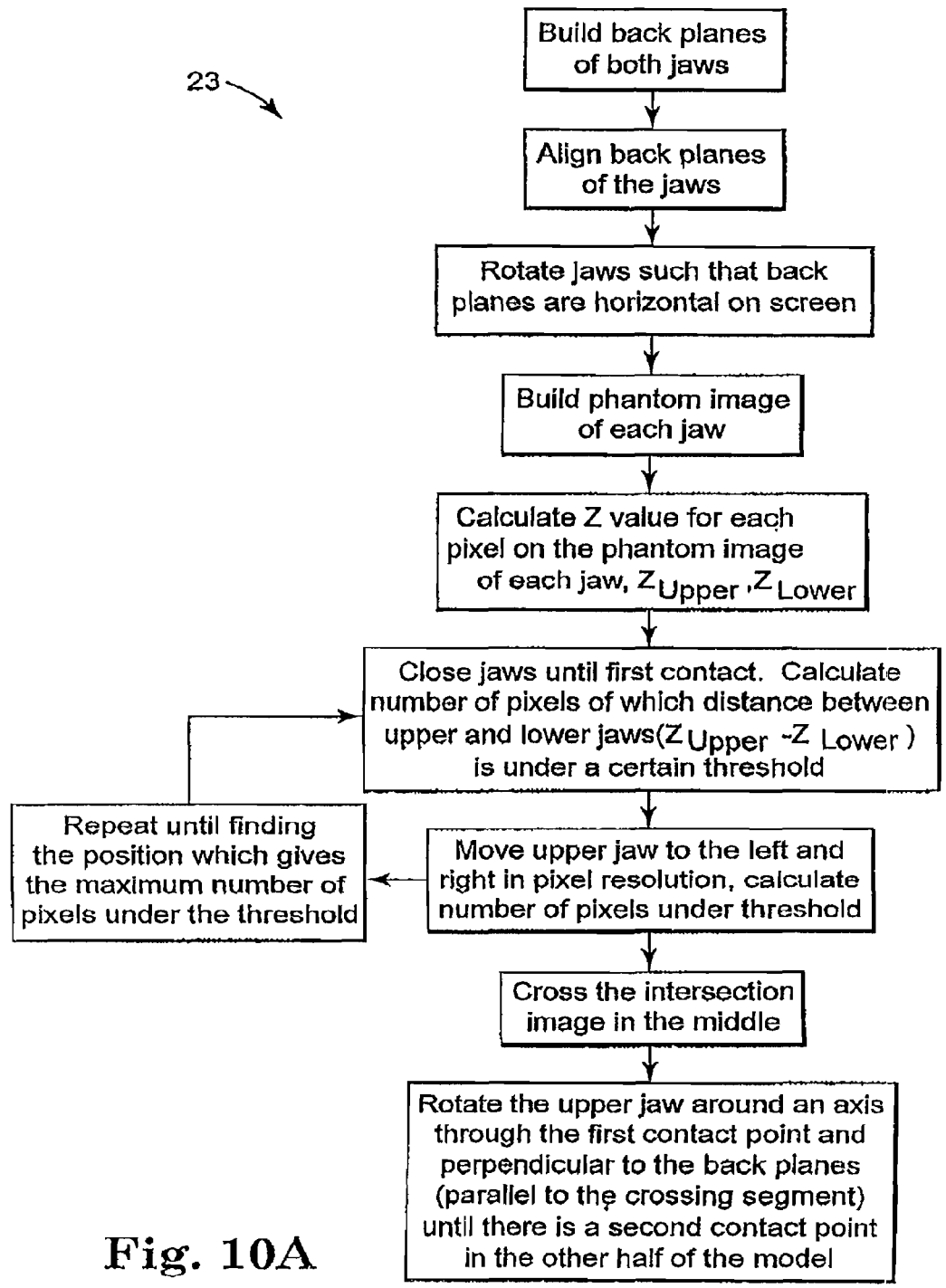
FIG. 10A shows a flow diagram of a bite registration algorithm for use in providing optimal occlusal relationship in accordance with the present invention and FIGS. 10B and 10C show screen displays for use in describing the algorithm.
Figure 10B:
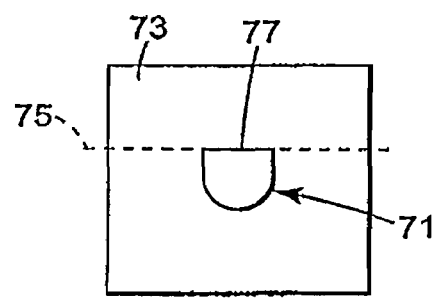
Figure 10C:
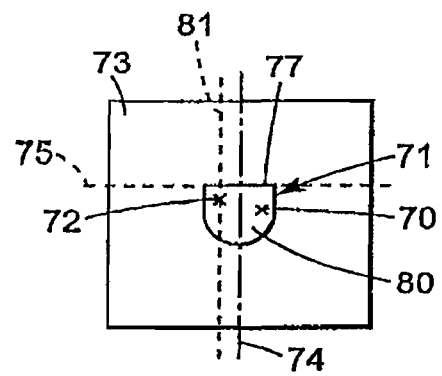

FIGS. 10A-10C shows an illustrative example including use of the wobbling technique 23. First, back planes 77 of both an upper and lower dental arch are created and the back planes 77 are aligned along an alignment plane 75. For example, such alignment of the back planes may be performed as described with reference to FIGS. 6A and 6B. Thereafter, the upper and lower dental arches are rotated as shown by the dental model 71 on screen 73 such that the back planes are horizontal on the screen 73 corresponding to alignment plane 75 as shown in FIG. 10B.

With the back planes 77 so aligned, phantom images of the upper and lower dental arch images are generated, i.e., images not displayed but which preferably include only measured digital data representative of dental arch images. A Z value for each pixel on the phantom image of each of the upper and lower phantom arch images is calculated, i.e., $Z_{upper}$, $Z_{lower}$. In this particular illustrative embodiment, the Z value is a z coordinate value for each pixel as the back planes 77 are aligned along the z-coordinate plane.

The upper and lower phantom arch images are then moved closer to one another until a first contact point 72 is detected (FIG. 10C). After contact is attained, a comparison of Z values for corresponding pixels in the upper and lower phantom arch images is performed. The comparison includes calculating the distance between the corresponding pixels by taking the difference between $Z_{upper}$ and $Z_{lower}$. The number of corresponding pixels in the upper and lower dental arch images having a distance therebetween below a certain threshold is then generated, i.e., N1.

The upper dental arch image is then moved to the right and to the left of the first contact point in pixel resolution, preferably one pixel. The number of corresponding pixels in the upper and lower dental arch images having a distance therebetween that is below the threshold is then generated for the positions of the upper dental image at the right and left of the first contact point, i.e., N2 and N3. N2 and N3 are compared to N1 to determine if the position of the upper dental arch corresponding to N2 or N3 is a more optimal position than N1, i.e., the best or optimal position being the position corresponding to the maximum number of corresponding pixels having a distance therebetween that fall below the threshold. The process of movement to the right or left of the more optimal position is repeated and calculations are continued until the position corresponding to the maximum number of corresponding pixels having a distance therebetween that is below the threshold is attained.

With the position of the upper dental arch image attained corresponding to the maximum number of corresponding pixels having a distance therebetween that is below the threshold, the dental model including the upper and lower arch images is segmented symmetrically, i.e., in the middle, by plane 74 lying perpendicular to the alignment plane 75 as shown in FIG. 10C. The symmetrically segmented dental model 71 includes first half 79 and second half 80 with the first point of contact 72 lying in the first half 79. The upper dental arch image is then rotated around an axis 81 extending through the first contact point 72 and perpendicular to the back planes 77 or alignment plane 75, i.e., parallel to the segmenting plane 74. The rotation is continued until there is a second contact point 70 attained in the second half 80 of the dental model. When the second contact point is attained, the optimal alignment position, i.e., occlusal relationship, of the upper and lower dental arch images is achieved. Thereafter, upon attachment of the condyle axis to the aligned upper and lower dental arch images, and optionally attachment of the condyle geometry data, the dental model is saved, i.e., the file structure for the dental model is generated.

Figure 12A:
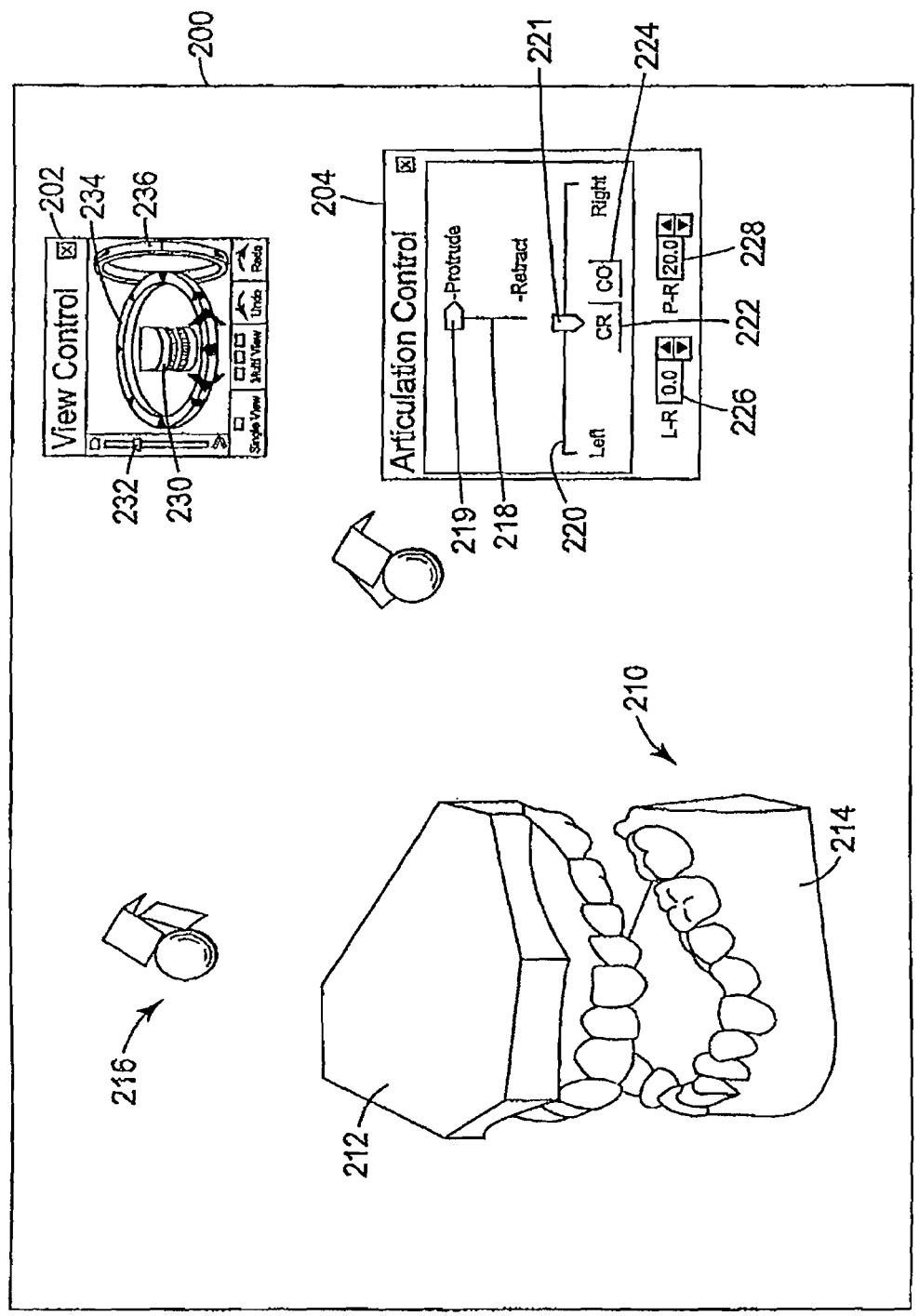
FIGS. 12A and 12B are illustrations of a graphic user interface provided by the dental articulation program of FIG. 1.
Figure 12B:
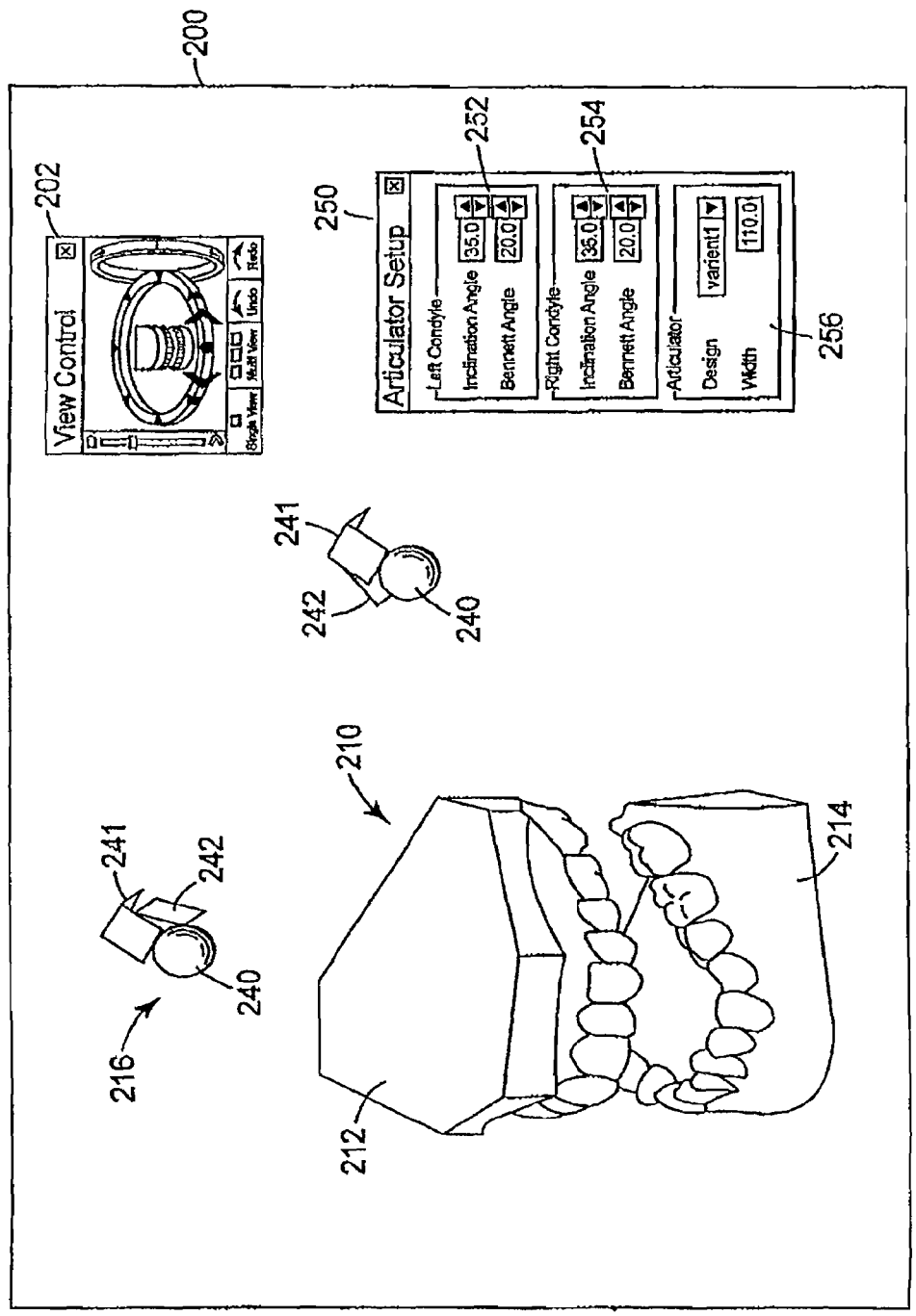

FIGS. 12A and 12B are illustrations of one embodiment of a graphic user interface provided by the dental articulation user program 20 of FIG. 1. If the condyle geometry is not already a part of the dental model 210, the articulation interface may include input of condyle geometry data as shown in FIG. 12B, in addition to the hinge axis data as represented in the model 210 by spheres 240. The hinge axis is preferably a line segment connecting the center of the condyles. In other words, the hinge axis represents the position of the condyles of the patient. FIG. 12B shows an articulator setup interface 250 with a view control interface 202 to be described in general below. The setup interface 250 includes a left condyle input section 252 and a right condyle input section 254 which mimics the geometry used in mechanical articulators; such mechanical articulators typically have several adjustments. Such common adjustments include the inclination of the fossa, i.e., the inclination angle, as shown by the right angle member 241 on the model 210, and also the Bennett angle as represented by the plane member 242 on the model 210. Further, such adjustments may include various other input data, such as the width or distance between the condyles as shown in the other input section 256. As shown by the general nature of section 256, the other various adjustment factors may depend on the type of articulator the user is trying to mimic.

Therefore, the condyle geometry can be approximated by such simple inputs into such input interface sections. These inputs can be based on data such as population norms or patient specific data. Preferably, the condyle geometry is generated from clinical measurements and is the condyle geometry data which has previously been described with reference to at least FIG. 1.

The screen display 200 of FIG. 12A shows a dental model 210 including upper dental arch 212, lower dental arch 214, and condyle hinge axis 216. The display further provides the view control interface 202 and an articulation control interface 204 for allowing the user to manipulate the dental model 210 as desired. The view control interface 202 includes model icon 230 at the center of the interface with a first set plane rotation element 234 thereabout, and a second set plane rotation element 236 to the left of the first set plane rotation element 234. The first and second set plane rotation elements allow the user to rotate the model within the set planes. Further, the view control interface 202 includes a slide control 232 for allowing the user to move the jaws relative to one another. For example, the interface may allow the user to move at least one of the upper and lower dental arches relative to the reference hinge axis or further, for example, the interface may allow the user to hold the upper dental arch in a fixed position with the lower arch being moved relative to the upper arch and the reference hinge axis. A view control interface such as interface 202 is described in Israeli Patent Application No. 120867 entitled "Computer User Interface For Orthodontic Use" filed May, 20, 1997 and assigned to Cadent, Ltd. (Israel) which is hereby entirely incorporated by reference herein.

Articulation control interface 204 includes protrude/retract slide control 218 for allowing the user to move the lower dental arch 214 relative to the upper dental arch 212. For example, if the slide control button 219 is positioned at the far end of the slide by the protrude text as shown in FIG. 12A, the lower dental arch 214 is in a maximum protrude state relative to the upper dental arch 212. When the slide control button 219 is moved towards the retract portion of the slide control 218, the lower dental arch 214 is in a retracted state relative to the upper dental arch 212.

Further, the articulation control interface 204 includes a left/right slide control 220 for use in sliding the lower dental arch 214 relative to the upper dental arch 212 in a direction along the hinge axis 216. The actual lateral position of the lower arch relative to the upper arch is dependent on the position of slide button 221 relative to the ends of the slide control 220.

The protruded or retracted position or the left or right sliding position of the lower and upper dental arches may also be controlled using dimensional changes provided by the user per inputs 228 and 226, respectively. For example, if the lower dental arch 214 is to be slid 3 mm to the right relative to the upper dental arch 212, then 3 would be selected for input 226.

Further, the interface 204 includes centric relation button 222 and centric occlusion button 224. Selection of the centric relation button 222 moves the dental arches 212, 214 relative to the hinge axis 216 to a position representative of when the condyles of the patient are fully seated in the patient's fossas. The position of the model as stored upon creation is the centric occlusion position, i.e., the originating position. In other words, when the model is first brought up on the screen 200, the model is in centric occlusion. To show the position of the model when in centric relation, the button 222 is selected. For example, the position of the elements of the model in centric occlusion is the position of the model after undergoing optimization by the wobbling technique previously described. The position of the elements in centric relation is achieved by a three dimensional transformation of the model in centric occlusion using a delta measurement taken between the two positions such as with the use of a wax bite impression at centric occlusion relative to a wax bite impression at centric relation.

In other words, generally, the interface provided by the user program 20 provides the ability for the user to view the dental model at any angle and/or magnification. The viewing algorithms are controlled by mouse activations and/or a keyboard, or any other mechanism for selecting or initiating computing actions or manipulation of images on a screen as commonly used by one skilled in the art. Further, generally, the user is given the ability to manipulate the dental model for articulation, either simple hinge or full articulation. For example, the jaw can be opened and closed by rotating the lower arch about the hinge axis and/or the lower arch can be slid over the upper arch using the slide controls and collision detection, e.g., either simple contact detection or a more complex collision detection technique similar to the wobbling technique previously described herein. Further, for example, initial hinge opening may be performed from centric relation which involves rotation about the reference hinge axis of the model. When opening from positions other than centric relation, the motion of the condyles may include various rotations and translations (e.g., 6 degrees of freedom). In other words, in full articulation, 6 degree of freedom motion of the mandible relative to the cranium can be simulated. Such motions may be limited by the constraints of the condyle geometry and/or collision detection, also as previously described herein. The complex motions of the lower arch image (a rigid body connected to the condyles) relative to the upper arch image (a rigid body connected to the fossas) can be determined, such as based on 3D sensor data.

It should be readily apparent that the items shown in the display screen 200 are only a few of the numerous interface elements or icons that may be used with the present dental model. For example, other elements for bringing up the model, deleting a model, moving a model or any other elements typically used in graphic manipulation may be used according to the present invention. Further, the present invention is clearly not limited to those elements and techniques described or illustrated herein, but only as described in the accompanying claims. For example, the dental model may be manipulated to provide occlusal maps such as described in Israeli Patent Application No. 120892 entitled "Method For Obtaining a Dental Occlusion Map" filed May 22, 1997 and currently assigned to Cadent, Ltd. (Israel), hereby entirely incorporated by reference.

Figure 13:
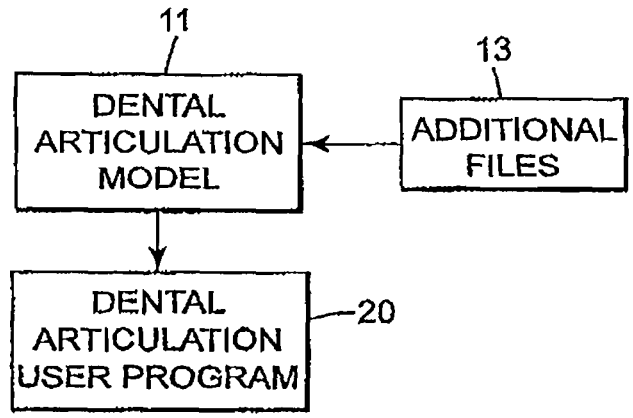
FIG. 13 is a block diagram illustration of the attachment of additional files to the dental model according to the present invention.
Figure 14:
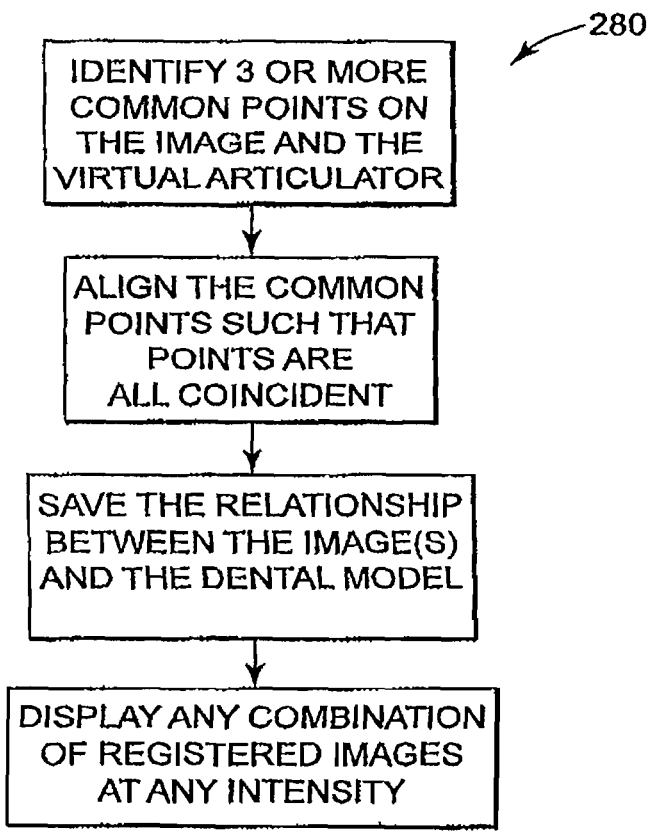
FIG. 14 is one embodiment of a method for attaching a graphics file representative of an image to the dental model along with use of such attached data.
Figure 15:
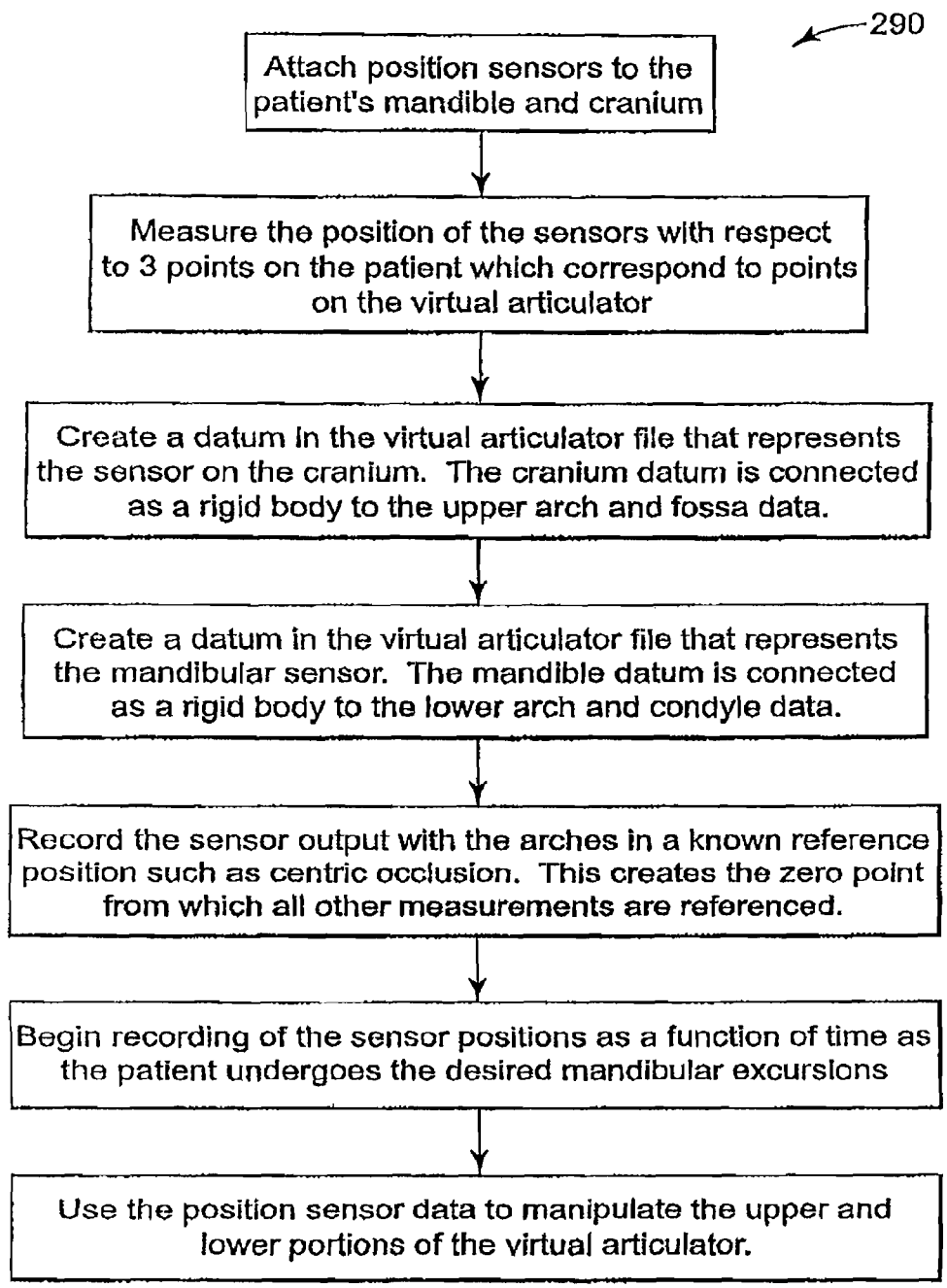
FIG. 15 is another embodiment of a method for attaching a file including motion data to the dental model along with use of such attached data.

FIG. 13 is a general block diagram illustration of an embodiment of the present invention in which additional graphics files 13 are attached to the dental model 11 according to the present invention. The attached additional graphics files 13 can then be used under control of the dental articulation user program 20 and interface provided thereby. FIGS. 14 and 15 illustrate two techniques for attachment and use of such graphics files according to the present invention.

An image attachment method 280 is shown in FIG. 14. The use of the images attached via this method 280 is further illustrated in FIGS. 16A and 16B. In the image attachment method 280, an image (e.g., any two or three dimensional image) is digitized. For example, the images may be from cephalometric x-rays, panoramic x-rays, patient photographs, intraoral photographs, and/or three dimensional scans of patients (e.g., using Vivid 700 Digitizer available from Minolta Corp., Ramsey, N.J.). Three or more common points between the image and the dental model or articulation model are identified. The three or more common points between the image and the dental model are then aligned to register the image to the dental model. For example, one pair of common points may be first aligned and then the image may be scaled and rotated relative to the dental model such that all the identified common points are coincident. The relationship between the image and the dental model is then saved and provides a unified model of the patient which is useful for diagnosis. Thereafter, the dental model and the image may be displayed in any combination of registered images at any intensity. For example, one image can be faded out while the other fades in to view corresponding features. Even more simply, the image may be of a different intensity than the dental model.

Figure 16A:
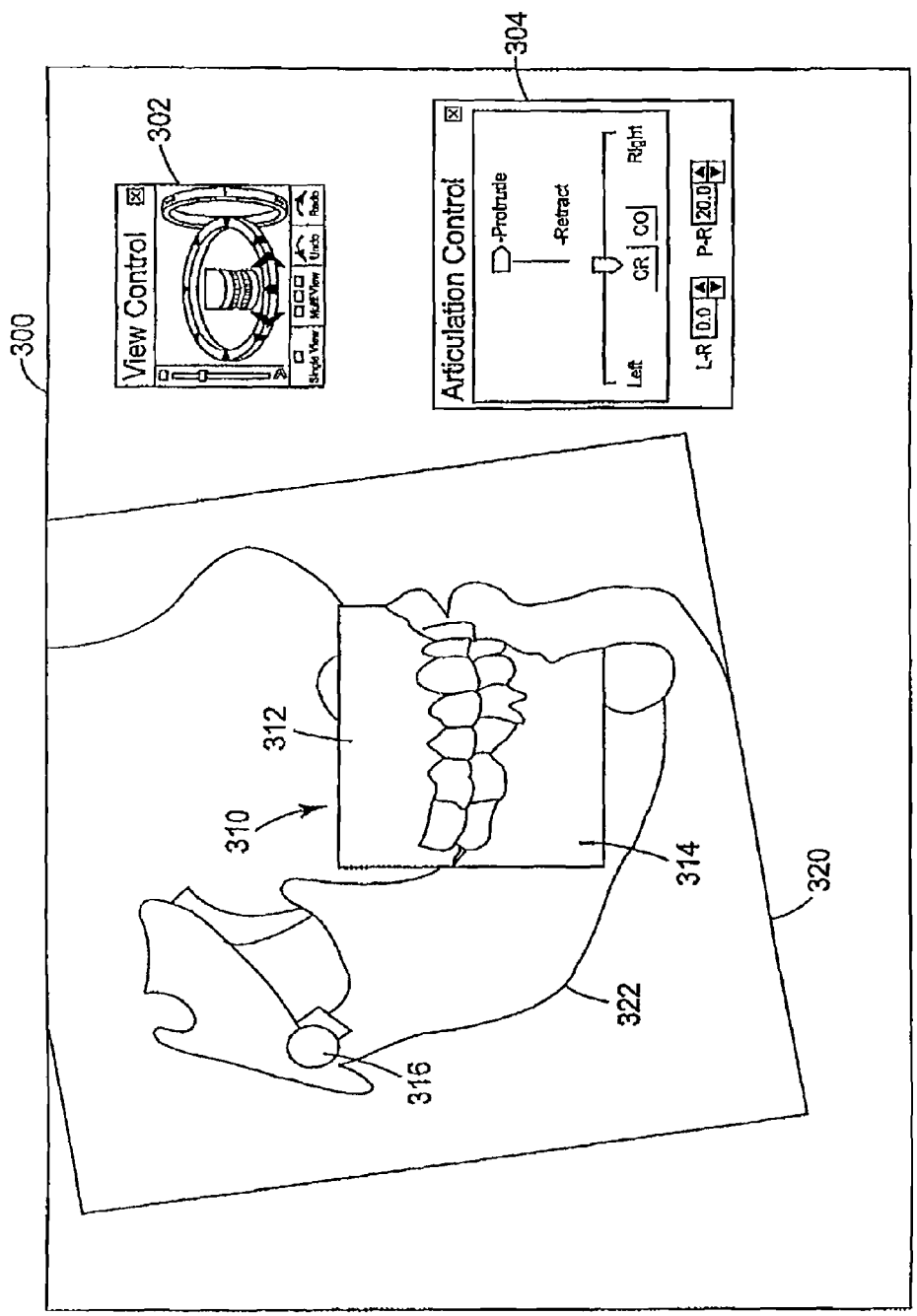
FIGS. 16A and 16B are graphic user interface illustrations showing the display of information of the graphics file resulting from the method of FIG. 14.
Figure 16B:
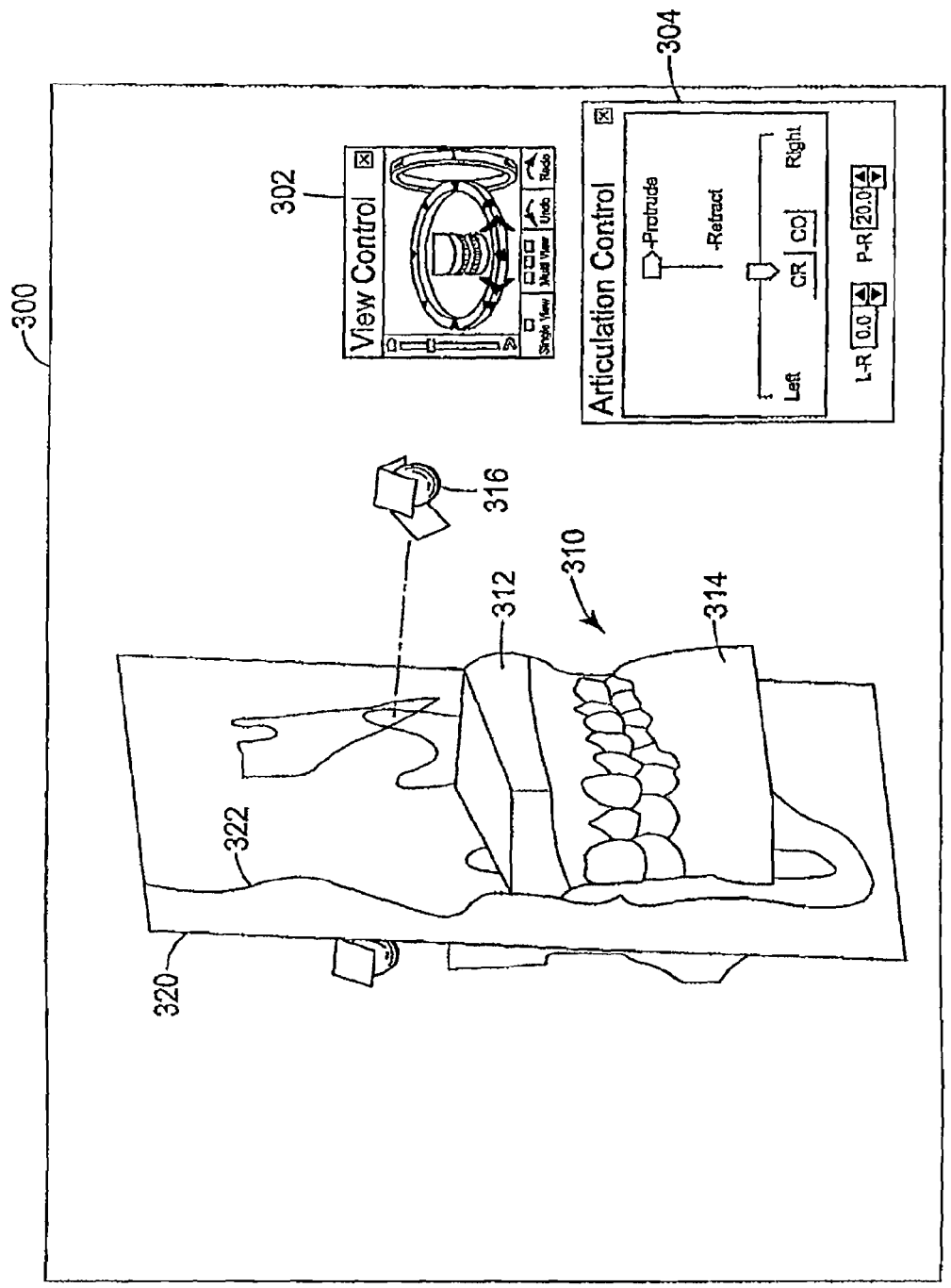

One example of a digitized cephalometric x-ray image 320 having tracings 322 thereon is shown in FIG. 16A on display screen 300. The x-ray image 320 is attached or registered with dental model 310 including upper and lower dental arches 312, 314, and condyle axis 316. As further shown, the dental model 310 with attached x-ray image 320 can then be manipulated by view control interface 302 and articulation control interface 304 as desired by the user and as previously described above. In FIG. 16B, the dental model 310 with the attached x-ray image 320 is shown rotated from its previous position shown in FIG. 16A.

A method 290 of attaching a graphics file including motion data to the dental model is shown in the block diagram of FIG. 15. First, the motion of the mandible is recorded for later playback using the dental model. To record the motion of the mandible, position sensors are attached to the patient's mandible and cranium. For example, such sensors may be sensors available under the trade designation of Minibird 6 degree of freedom sensors from Ascension Technology, Burlington, Vt. The position of the sensor on the cranium is measured with respect to three points on the patient which correspond to identifiable points on the dental model. i.e., the virtual articulator model. For example, such points may be the incisor tip, left and right condyle, etc. The position of the sensor on the mandible is also measured from three points on the patient that correspond to three identifiable points on the dental model. Such measurements may be made with a device like the Microscribe-3DX digitizer.

Thereafter, a datum representing the sensor on the cranium is created for attachment to the dental model file for use in virtual articulation. The cranium sensor datum is connected as a rigid body to the upper dental arch and fossa data of the condyle geometry. Likewise, a datum representing the sensor on the mandible is created for attachment to the dental model file for use in virtual articulation. The mandible sensor datum is connected as a rigid body to the lower dental arch and condyle data of the condyle geometry previously provided for the patient.

Using a computer implemented system, or any other suitable recording apparatus, the sensor output of the cranium and mandible sensors are recorded at a known reference position. For example, the known reference position may be a position with the arches in centric occlusion, in centric relation, etc. This creates an initial reference measurement position or a zero point from which all other measurements of the sensor outputs are made and referenced. With the known reference measurement position established, the sensor positions are recorded as a function of time as the patient undergoes desired mandibular excursions.

The data recorded is saved to a file for attachment to the dental articulation model. The recorded data representative of the motion of the mandible, i.e., the position sensor data, is used to manipulate the upper and lower dental arches of the dental model for articulation. The recorded data is applied to the sensor location points on the upper and lower dental arches of the dental model using rigid body graphic transformations as the cranium sensor datum and the mandible sensor datum are connected as a rigid body to the upper arch and lower arch respectively. The recorded data can be used to play back the mandibular motion to a user of the dental articulation model in real time, i.e., substantially at the same time as the data is recorded, at a later time, in slow motion, reverse, etc. as would be known to one skilled in the art. Further, in accordance with the other aspects of the present invention, the dental model being played back with the mandibular motion may be viewed from various angles, at various zoom levels, etc. as the data is being played back.

It should be apparent to one skilled in the art, that if the cranium of the patient is fixed in placed during measurements used to sense the motion of the patient's mandible, or if the mandibular sensor is directly referenced to the cranium, then only the mandibular sensor is required to obtain the necessary measurements for recording mandibular motion. For example, in such a circumstance, only measurements using the mandibular sensor output and application of the recorded data to the location points on the lower arch are required to play back the mandibular motion using the dental model.

All references and patents disclosed herein are incorporated by reference in their entirety, as if each were individually incorporated. Various modifications and alterations of this invention will become apparent to those skilled in the art without departing from the scope of the invention, and it should be understood that this invention is not to be unduly limited to the illustrative embodiments and processes set forth herein.

What is claimed is:

1. A computerized method of creating a dental model for use in dental articulation, the method being implemented by a computer system and comprising:
   providing a first set of digital data corresponding to an upper arch image of at least a portion of an upper dental arch of a patient;
   providing a second set of digital data corresponding to a lower arch image of at least a portion of a lower dental arch of the patient;
   providing hinge axis data representative of the spatial orientation of at least one of the upper and lower dental arches relative to a hinge axis of the patient;
   providing bite alignment data representative of the spatial relationship between the upper dental arch and the lower dental arch of the patient;
   aligning the upper arch image and the lower arch image based on the bite alignment data and creating a reference hinge axis relative to the aligned upper and lower arch images based on the hinge axis data, wherein aligning the upper arch image and the lower arch image and creating the reference hinge axis comprises manipulating the first and second set of digital data until an aligned upper and lower arch image is attained;
   storing a third set of digital data representative of the aligned upper and lower arch images;
   determining a location of the reference hinge axis relative to the aligned upper and lower arch images in the same coordinate system as the aligned upper and lower arch images;
   storing a fourth set of digital data representative of the location of the reference hinge axis, wherein the third set of digital data is linked to the fourth set of digital data; and
   outputting the dental model from the computer system.

2. The method according to claim 1, wherein the method further comprises:
   displaying at least the upper and lower arch images; and
   manipulating the upper and lower arch images to move at least one of the upper and lower arch images relative to the reference hinge axis.

3. The method according to claim 2, wherein manipulating the upper and lower arch images comprises:
   retaining the upper arch image in a fixed position; and
   moving the lower arch image relative to the upper arch image.

4. The method of claim 1, wherein providing the hinge axis data comprises:
   providing a two-dimensional image perpendicular to the hinge axis of the patient, the two-dimensional image representative of at least a portion of at least one of the upper and lower dental arches of the patient;
   locating the center of the condyle of the patient on the two-dimensional image;
   locating two or more identifiable locations of at least one of the upper and lower dental arches on the two-dimensional image; and
   determining the spatial coordinates of the two or more identifiable locations from the center of the condyle, wherein the reference hinge axis is created based on the spatial coordinates and digital data representative of locations of the upper and lower arch images corresponding to the two or more identifiable locations on the two-dimensional image.

5. The method according to claim 1, wherein providing the hinge axis data comprises using a facebow apparatus to provide at least one set of indicia representative of the spatial orientation of the upper dental arch of the patient relative to the hinge axis of the patient.

6. The method according to claim 1, wherein providing hinge axis data further comprises:
   providing coordinates of at least three identifiable positions on the upper dental arch of the patient;
   identifying at least three positions on the upper arch image corresponding to the identifiable positions; and
   determining the spatial coordinates of the at least three positions on the upper arch image, wherein the reference hinge axis is created based on digital data representative of the spatial coordinates and the at least one set of indicia.

7. The method according to claim 1, wherein providing bite alignment data comprises providing data representative of at least one common geometrical feature of both the upper and lower arch images.

8. The method according to claim 7, wherein providing data representative of a common geometrical feature comprises:
   providing impressions of the upper and lower dental arches of the patient;
   providing a bite impression of the patient;
   aligning the upper and lower impressions with the bite impression;
   creating the at least one common feature in the impressions of the upper and lower dental arches; and
   digitizing the impressions of the upper and lower dental arches resulting in the first and second set of digital data corresponding to the upper and lower arch images and further resulting in bite alignment data representative of the at least one common feature, wherein the upper arch image and lower arch image are aligned based on the bite alignment data representative of the at least one common feature.

9. The method according to claim 8, wherein the at least one common feature comprises a line and a plane perpendicular to the occlusal plane.

10. The method according to claim 1, wherein providing bite alignment data comprises capturing spatial coordinates of at least three nonlinear positions of each of the upper and lower dental arches of the patient.

11. The method according to claim 10, wherein aligning the upper arch image and the lower arch image comprises:
   identifying positions of the upper and lower arch images corresponding to each of the at least three nonlinear positions of the upper and lower dental arches of the patient; and
   aligning the upper and lower arch images by bringing the identified positions of the upper and lower arch images into the same relationship as the spatial coordinates for the at least three nonlinear positions of each of the upper and lower dental arches of the patient.

12. The method according to claim 10, wherein providing spatial coordinates comprises capturing the spatial coordinates for the at least three nonlinear positions of each of the upper and lower dental arches of the patient directly from the patient.

13. The method according to claim 10, wherein providing spatial coordinates comprises capturing the spatial coordinates for the at least three nonlinear positions of each of the upper and lower dental arches from a bite impression of the patient.

14. The method according to claim 1, wherein the method further comprises providing data associated with condyle geometry of the patient.

15. The method according to claim 14, wherein the method further comprises:
   displaying at least the upper and lower arch images; and
   manipulating the upper and lower arch images to move the lower arch image relative to the upper arch image and the reference hinge axis, wherein the condyle geometry data provides limitations on the movement of at least the lower arch.

* * * * *